United States Patent [19]
Fan et al.

[11] Patent Number: 5,968,780
[45] Date of Patent: Oct. 19, 1999

[54] DENDRITIC CELL-DERIVED GROWTH FACTOR

[75] Inventors: Ping Fan, Gaithersburg, Md.; Daniel R. Soppet, Centreville, Va.; Yi Li, Sunnyvale; Patrick J. Dillon, Carlsbad, both of Calif.

[73] Assignee: Human Genome Sciences, Inc., Rockville, Md.

[21] Appl. No.: 09/019,201

[22] Filed: Feb. 5, 1998

Related U.S. Application Data

[60] Provisional application No. 60/038,829, Feb. 6, 1997.

[51] Int. Cl.$^6$ .............................. C12N 15/16; C12N 1/21; C12N 5/10; C12N 15/63
[52] U.S. Cl. ..................... 435/69.4; 435/455; 435/325; 435/252.3; 435/254.11; 435/320.1; 536/23.1; 536/23.5; 536/23.51; 536/24.1; 536/24.3; 536/24.31; 536/24.33
[58] Field of Search .................................. 536/23.1, 23.5, 536/23.51, 24.1, 24.3, 24.31, 24.33; 435/69.1, 69.4, 455, 325, 252.3, 254.11, 320.1

[56] References Cited

FOREIGN PATENT DOCUMENTS

91/18620 12/1991 WIPO .
95/28479 10/1995 WIPO .

OTHER PUBLICATIONS

Database Embl, Accession No. G10193, Aug. 17, 1995.
Database Embl, Accession No. U41528, Dec. 9, 1995.
Mohamadzadeh, M. et al., J. of Immun., 156 (9):3102–3106 (May 1, 1996).
Homma, K. et al., J. of Biol. Chem., 271:13770–13775 (1996).
Genbank Acc. No. AA081788 (Oct. 1996).
Genbank Acc. No. R50107 (May 1995).
Genbank Acc. No. R98295 (Sep. 1995).

*Primary Examiner*—Elizabeth Kemmerer
*Attorney, Agent, or Firm*—Kenley K. Hoover

[57] ABSTRACT

The present invention relates to a novel DCDGF protein which is a member of a novel family of growth factors of which the prototype is called Insect-Derived Growth Factor (IDGF). In particular, isolated nucleic acid molecules are provided encoding the human DCDGF protein. DCDGF polypeptides are also provided as are vectors, host cells and recombinant methods for producing the same. The invention further relates to screening methods for identifying agonists and antagonists of DCDGF activity. Also provided are diagnostic methods for diagnosing DiGeorge Syndrome and, particularly, immune system-related disorders. and therapeutic methods for treating immune system-related disorders.

112 Claims, 5 Drawing Sheets

Figure 1A

```
-133  TCGACCCACGCGTCCGGCTTTTCCGGTGCTCTGCACAGATGCTGGGGCGCTGAGCAAACA  -74

-73  GCCCTCAGTTTCTGGAGCTGTTCCGAGTCCCGTGGAGTCTCCATCTGAGCCCTTTCCTAG  -14

-13  TCCAGGCATCCCGATGTTGGTGGATGGCCCATCTGAGCGGCCAGCCCTGTGCTTCTTGCT   46
   1                M  L  V  D  G  P  S  E  R  P  A  L  C  F  L  L   16

47  GTTGGCTGTGGCAATGTCTTTCTTCGGCTCAGCTCTATCCATAGATGAAACACGGGCGCA  106
  17   L  A  V  A  M  S  F  F  G  S  A  L  S  I  D  E  T  R  A  H   36

107  TCTGTTGTTGAAAGAAAAGATGATGCGGCTGGGGGGCGGCTGGTGCTGAATACCAAGGA   166
  37   L  L  L  K  E  K  M  M  R  L  G  G  R  L  V  L  N  T  K  E    56

167  GGAGCTGGCCAATGAGAGGCTCATGACGCTCAAAATCGCTGAGATGAAGGAGGCCATGAG  226
  57   E  L  A  N  E  R  L  M  T  L  K  I  A  E  M  K  E  A  M  R    76

227  GACCCTGATATTCCCACCCAGCATGCACTTTTTCCAGGCCAAGCATCTCATTGAGAGAAG  286
  77   T  L  I  F  P  P  S  M  H  F  F  Q  A  K  H  L  I  E  R  S    96

287  TCAAGTGTTTAATATTCTAAGGATGATGCCAAAAGGGGCTGCCTTGCACCTCCATGACAT  346
  97   Q  V  F  N  I  L  R  M  M  P  K  G  A  A  L  H  L  H  D  I   116

347  TGGCATCGTGACTATGGACTGGCTGGTGAGGAATGTCACCTACAGGCCTCACTGCCACAT  406
 117   G  I  V  T  M  D  W  L  V  R  N  V  T  Y  R  P  H  C  H  I   136

407  CTGTTTCACCCCAAGGGGGATCATGCAGTTCAGATTTGCTCACCCAACTCCCCGTCCATC  466
 137   C  F  T  P  R  G  I  M  Q  F  R  F  A  H  P  T  P  R  P  S   156

467  AGAAAAATGTTCCAAGTGGATTCTGCTGGAGGATTATCGGAAGCGGGTGCAGAACGTCAC  526
 157   E  K  C  S  K  W  I  L  L  E  D  Y  R  K  R  V  Q  N  V  T   176

527  TGAGTTTGATGACAGCTTGCTGAGGAATTTCACTCTGGTGACCCAGCACCCGGAGGTGAT  586
 177   E  F  D  D  S  L  L  R  N  F  T  L  V  T  Q  H  P  E  V  I   196

587  TTACACAAACCAAAATGTTGTCTGGTCGAAATTTGAAACCATCTTCTTCACCATCTCTGG  646
 197   Y  T  N  Q  N  V  V  W  S  K  F  E  T  I  F  F  T  I  S  G   216

647  TCTCATCCATTACGCACCAGTGTTCAGAGACTATGTCTTCCGGAGCATGCAGGAGTTCTA  706
 217   L  I  H  Y  A  P  V  F  R  D  Y  V  F  R  S  M  Q  E  F  Y   236

707  CGAGGACAACGTGCTCTACATGGAGATCAGAGCCAGGCTGCTGCCGGTGTATGAGCTCAG  766
 237   E  D  N  V  L  Y  M  E  I  R  A  R  L  L  P  V  Y  E  L  S   256

767  TGGAGAGCACCATGACGAAGAGTGGTCAGTGAAGACTTACCAGGAAGTAGCTCAGAAGTT  826
 257   G  E  H  H  D  E  E  W  S  V  K  T  Y  Q  E  V  A  Q  K  F   276

827  TGTGGAAACTCACCCTGAGTTTATTGGAATCAAAATCATTTATTCGGATCACAGATCCAA  886
 277   V  E  T  H  P  E  F  I  G  I  K  I  I  Y  S  D  H  R  S  K   296

887  AGATGTGGCTGTCATCGCAGAATCCATCCGAATGGCCATGGGGCTCCGAATCAAGTTCCC  946
 297   D  V  A  V  I  A  E  S  I  R  M  A  M  G  L  R  I  K  F  P   316

947  CACGGTGGTGGCAGGGTTTGACCTGGTGGGGCATGAGGACACTGGCCACTCCTTGCGTGA  1006
 317   T  V  V  A  G  F  D  L  V  G  H  E  D  T  G  H  S  L  R  D   336
```

Figure 1B

```
1007 CTACAAGGAAGCTCTGATGATCCCCGCCAAGGATGGCGTTAAGCTGCCTTACTTCTTCCA 1066
 337   Y  K  E  A  L  M  I  P  A  K  D  G  V  K  L  P  Y  F  F  H   356

1067 CGCCGGAGAAACAGACTGGCAGGGTACTTCCATAGACAGGAACATTCTGGATGCTCTGAT 1126
 357   A  G  E  T  D  W  Q  G  T  S  I  D  R  N  I  L  D  A  L  M   376

1127 GCTGAACACTACCAGAATCGGCCATGGATTTGCTTTGAGCAAACACCCCGCAGTCAGGAC 1186
 377   L  N  T  T  R  I  G  H  G  F  A  L  S  K  H  P  A  V  R  T   396

1187 TTACTCCTGGAAAAAGGACATCCCCATAGAAGTCTGTCCCATCTCTAACCAGGTGCTGAA 1246
 397   Y  S  W  K  K  D  I  P  I  E  V  C  P  I  S  N  Q  V  L  K   416

1247 ACTGGTGTCTGACTTGAGGAACCACCCTGTAGCCACTCTGATGGCCACTGGGCACCCCAT 1306
 417   L  V  S  D  L  R  N  H  P  V  A  T  L  M  A  T  G  H  P  M   436

1307 GGTGATCAGCTCTGATGACCCAGCTATGTTTGGTGCCAAAGGCTTGTCCTATGATTTCTA 1366
 437   V  I  S  S  D  D  P  A  M  F  G  A  K  G  L  S  Y  D  F  Y   456

1367 TGAGGTCTTCATGGGCATTGGGGGGATGAAGGCTGACCTGAGGACCCTCAAACAGCTGGC 1426
 457   E  V  F  M  G  I  G  G  M  K  A  D  L  R  T  L  K  Q  L  A   476

1427 CATGAACTCTATCAAGTACAGTACCCTGTTGGAGAGTGAGAAAAATACTTCCATGGAAAT 1486
 477   M  N  S  I  K  Y  S  T  L  L  E  S  E  K  N  T  S  M  E  I   496

1487 CTGGAAGAAGAGATGGGATAAGTTCATAGCAGATGTGGCTACAAAGTGAGGAGAAGCTAG 1546
 497   W  K  K  R  W  D  K  F  I  A  D  V  A  T  K  *                511

1547 CCAGCCCTCTACAAGCTGTCTTCTTGCACACGCTGTCACTTCCTCTCACTCGTTCTTGAA 1606

1607 TCAGCTCCATGTGCCCATGAAATCAATGGCCTCTGTATGGAGCGACCCTGTGAGAAGCAC 1666

1667 TTGGCTGGCTGAACAAATTCATCCTCTGGAAATATTCTCTCTCAGCCACAGTGACATTGA 1726

1727 CCTCTTGGTTTTCTCCTCTCTCTGGCCATTTCTTCCAGTTTCCCTATTTCAGAGTCTTCT 1786

1787 CCTCTCTCTGATCTCTGTGCTGTTTCCTCAGGACTCAGTCCTGGGCTCTCTTCTATTCTG 1846

1847 GTCTCTTTATTTTTTATTTTTGTATTTTTTCGAGATGGAGTTTTGCTCTTGTTGCCCAG 1906

1907 GCTGGAGTACAATGGTGCGATCTCAGCTCAGTGCAACCTCCGCCACCCGGGTTCAGGCAA 1966

1967 TTCTCTTGCATCAGCCTCGCGAGTAGTTGGAATTATAGGCATGTGCCACCACACCCAGCT 2026

2027 GATTTTTGCATTTTTAGTAGAGACAGGTTTTCACCATGTTGGCGAGGCTGGTATCCAACT 2086

2087 CTTGACCTCAGGTGATCCACTCGCCCCTTGGCTCCCAAAGTGCTGGAATTACAGGCATTA 2146

2147 GCCACCATGCCTGGCCTATTCTGGTCTCTTTAACTCTCTCCTCTTTATTTCTCTTCTCTC 2206

2207 TCTGTACACTTTTCCTGGGTGGTCTCATCCATTCCTTTGCTTTTTCATACCATTTATTTG 2266

2267 TTAATGATTCCCACATTTATTTATGCACTTGGAGAGCTCACAGGAATCTCAGAAACTGAT 2326
```

Figure 1C

```
2327  GAGGTACAATTCTGAACCCTCAGTCTCTTCCCTTTAAACCTTTCTTTTTCTCTACTTTAA  2386
2387  TTTTTCTAAAGANTGTCTTGCTATGTTGCCCAGGCTGGTCTCCAACTCAAGTGATCCTCC  2446
2447  TGCCGCAGTCTCCCGAAGTGCTGGGATTACTGACATGAGCCACCACACTCAGCCCTTTAA  2506
2507  ACCTTTCCCTGGCCTTTCCCATAGCTGGTGAAGGACACCTCCATCCATTCCACGCAGTTG  2566
2567  CTCAAAGCAGAAATTTTCAGTGCAAGTCTTGATGCTGCGCCGTCCCCACTCCCTACATC  2626
2627  AGAACGCATCCCTCATCTGGACTCCAGCGGTGGCTTCTTGATGCTGCGCGGTCCCCCACT  2686
2687  CCCTACATCAGAATGCATCCCGCATCCAGACTCCAGCGGTGGTGCTCTACCTGCACGCTG  2746
2747  TTGCCAAGTCCAAGCTACCATACTCCTGCCTGAGCTATGACAACAGCCTCCTCACTGATC  2806
2807  TCCCCTTTCTTCCCTTTGCCTCCTCCAGCTCATTTTTCACAGTGGTAGAATGACATTTTG  2866
2867  TTTGTTTGTTTTGTTTTGTTTGGGATGGAGTCTCGCTCTGTTGCCCAGGGTGGAGTGCAG  2926
2927  CGGTGCGATCTCGGCTCACTGCAACCTCCACCTCCCGGGTTCAGGCGGATTCTCGTGCCT  2986
2987  CAGCCTCCTGAGTAGCTGGGATTACAGGCATGCACCACCATGCCCGGATAATTTTTGTGT  3046
3047  TTTTAGTAAAAATGGGGTTTCACTGTGTTGGCAGGCTGGTCTCGAACACCTGACTCGTGG  3106
3107  TCCACCCGCCTCGGCCTCCCAAAGCACTGGGATTGCAGGCGTNAGCCACCCGGNCTGNCC  3166
3167  TAGAATAGACTTTTAGAANATCAAAATANATCAGGTGTCTCCTTCGCATACNACNCNCTN  3226
3227  CGTCCANANGTACACCCCATGTCTCCACNGGGCATACACCATCCAATGTAATCTGGATTC  3286
3287  ATTCCGGCGCNTNCCTCTCNCANTNNATCANAGGGCCCCAACCCCGGCGGACNGTNCTNN  3346
3347  CTCAAANGTCCACNGCTCTATACCGTGCCTGNGTCTNTTCTCTTTCTCTCTNCCTGAAAA  3406
3407  NAGTCANTGNTTCTCTATNNNTCTTGCCCAATCCTGTTTANCCTAAATTTTCAAGTTCAA  3466
3467  TTTNNAGTCTCAGAAAAGTTNTCCTGTGNCCCCCANTTCTCNCANGAAAGCANGCCCCTT  3526
3527  GCCGC                                                         3531
```

Figure 2

```
  1 MLVDGPSERPALCFLLLAVAMSFFGSALSIDETR....AHLLLKEKMMR.  45
    ::.....  |:.|      :.    .::..  |: :.|    |.  |:: ::|
 16 VFAHNEARRASLRANHMVQHAPHIEPQASVIGGRPTPEAYNSLRDIFFRY  65

46 .....LGGRLVLNTKEELANERLMTLKIAEMKEAMRT.LIFPPSMHFFQA  89
         ||: :.|. ||  ||: :|. |. |  .|::  |   :|.|| |:|:.
 66 EESKTLGADITLTQKELQANQLIMEAKTREYEEGLATPHLFTPSQHLFEV 115

90 KHLIERSQVFNILRMMPKGAALHLHDIGIVTMDWLVRNVTYRPHCHIC.. 137
    . |..|.:|..:.  |||||.|| ||.:::..  |:|:|  :|||.:   :|
116 LDDIKQSPLFKYISSMPKGAVLHAHDTALCSTDFLIR.LTYRDNLWVCQG 164

138 FTPRGIMQFRFAHPTPRPSEKC.SKWILLEDYRKRVQNVTEFDDSLLRNF 186
    ..:::::.:||....|  .....  :.| ||..  |.  ::.....|.  |    ::
165 KGDKEVIGMRFSKTKPDVATQADCTWELLSKVRE.LHGADKVDTYLREHL 213

187 TLVTQHPEVIYTNQNVVWSKFETIFFTISGLIHYAPVFRDYVFRSMQEFY 236
    ||   .|.| : :.| .|..|:.||  :.|||:  ||| :  ||  :...:.||.
214 TL...YPTVKFLDNNEAWEQFGSIFALLDGLLFYAPSWADYYYNALKEFH 260

237 EDNVLYMEIRARLLPVYELSGEHHDEEWSVKTYQEVAQKFVETHPEFIGI 286
    .|.| |:|:|. |   :|:|.|.    .|  .|:.|.|.  :|::..| :|||
261 ADGVQYLEFRSTLPILYDLEGTSFTELDTVRIYKETLDKYMAEHIDFIGS 310

287 KIIYSDHRSKDVAVIAESIRMAMGLRIKFPTVVAGFDLVGHEDTGHSLRD 336
    |:||..  |..|  ..:.:  |::.:::: |:|..||||||||:|:.|:.|:|
311 KLIYAPIRNTDKEGLDNYIKVCVEIKEKYPDFVAGFDLVGQEEKGRPLKD 360

337 YKEALMIPAKDGVKLPYFFHAGETDWQGTSIDRNILDALMLNTTRIGHGF 386
    : ..|:   :.:    :.::|||||||:| |..:| |::||::|.|.||||||
361 FIPQLLGMPEN...IDFYFHAGETNWFGSTVDENLIDAVLLGTKRIGHGF 407

387 ALSKHPAVRTYSWKKDIPIEVCPISNQVLKLVSDLRNHPVATLMATGHPM 436
    ||  ||| |    ..::|:||| |||||||.||.|.||||.|  ::|...|:
408 ALVKHPLVLQMLKERNIAIEVNPISNQVLQLVADYRNHPCAYFFADNYPV 457

437 VISSDDPAMFGAKGLSYDFYEVFMGIGGMKADLRTLKQLAMNSIKYSTLL 486
    ||||||.:: |..||.||| .|:||:: ..|:| ||.||:|||.||.|
458 VISSDDPSFWKATPLSHDFYIAFLGIASAHSDMRLLKKLALNSINYSSLS 507

487 ESEKNTSMEIWKKRWDKFIADVAT 510
    ..:|....:. |. :||.||.:|  .
508 PEQKRVALAKWQIKWDDFIDEVLS 531
```

DENDRITIC CELL-DERIVED GROWTH FACTOR

This application claims benefit of 35 U.S.C. section 119(e) based on copending U.S. Provisional Application Serial No. 60/038,829, filed Feb. 6, 1997, which is hereby incorporated herein by reference.

FIELD OF THE INVENTION

The present invention relates to a human gene encoding a polypeptide which is a member of a novel growth factor family. More specifically, isolated nucleic acid molecules are provided encoding a human polypeptide named Dendritic Cell-Derived Growth Factor, hereinafter referred to as "DCDGF". DCDGF polypeptides are also provided, as are vectors, host cells and recombinant methods for producing the same. Also provided are diagnostic methods for detecting functional disorders of the immune system and developmental disorders of the immune and other systems, particularly DiGeorge Syndrome, and therapeutic methods for treating such disorders. The invention further relates to screening methods for identifying agonists and antagonists of DCDGF activity.

BACKGROUND OF THE INVENTION

Cellular growth and differentiation appear to be initiated, promoted, maintained and regulated by a multiplicity of stimulatory, inhibitory and synergistic factors and hormones. The alteration and/or breakdown of the cellular homeostasis mechanism seems to be a fundamental cause of growth related diseases, including neoplasia. Growth modulatory factors are implicated in a wide variety of pathological and physiological processes including signal transduction, cell communication, growth and development, embryogenesis, immune response, hematopoiesis cell survival and differentiation, inflammation, tissue repair and remodeling, atherosclerosis and cancer.

Several gene families are known to encode diverse groups of structurally and functionally related proteins referred to as "growth factors." One such growth factor family includes epidermal growth factor (EGF), transforming growth factor alpha (TGFα), betacellulin, amphiregulin, and vaccinia growth factor, which are growth and differentiation modulatory proteins produced by a variety of cell types, either under normal physiological conditions or in response to exogenous stimuli. These peptide growth factors influence cells through autocrine and paracrine mechanisms, playing important roles in normal wound healing in tissues such as skin, cornea and the gastrointestinal tract. They also share substantial amino acid sequence homology including the conserved placement of three intrachain disulfide bonds. In addition, all the factors of this EGF-related family bind to a 170,000 molecular weight transmembrane glycoprotein receptor and activate the tyrosine kinase activity in the receptor's cytoplasmic domain (Buhrow, S. A. et al., *J. Biol. Chem.*, 258:7824–7826 (1983)). The receptors are expressed by many types of cells including skin keratinocytes, fibroblasts, vascular endothelial cells, and epithelial cells of the GI tract.

The EGF-related peptide growth factors are synthesized by several cells involved in wound healing including platelets, keratinocytes, and activated macrophages. These growth factors have also been implicated in both the stimulation of growth and differentiation of certain cells, for example, in neoplasia, and the inhibition of other types of cells. For instance, betacellulin is a potent mitogen for retinal pigment epithelial cells and vascular smooth muscle cells. Amphiregulin is a bifunctional cell growth regulatory factor which exhibits potent inhibitory activity on DNA synthesis in neoplastic cells, yet promotes the growth of certain normal cells. A wide variety of uses for amphiregulin have been assigned including the treatment of wounds and cancers. For example, amphiregulin has potent anti-proliferative effects in vitro on several human cancer cell lines of epithelial origin. Amphiregulin also induces the proliferation of human foreskin fibroblasts as shown in U.S. Pat. No. 5,115,096. TGFα has pleiotropic biological effects and is synthesized by a number of oncogenically transformed, as well as by a variety of tumors, including renal, breast and squamous carcinomas, melanomas and glioblastomas. TGFα also plays a role in normal embryonic development and adult physiology and is expressed in many tissues including skin, brain, gastrointestinal mucosa and activating macrophages (Derynck, R. *Adv. Cancer Res.* 58:27–5 (1992)). Accordingly, TGFα is an important factor in controlling growth of epithelial cells and is important in wound healing, and it has also been found to be angiogenic (Schreiber, et al., *Science,* 2321250–1253 (1986)).

The transforming growth factor-beta (TGF-β) family of peptide growth factors includes five members, termed TGF-β1 through TGF-β5, all of which form homo-dimers of approximately 25 kDa. The TGF-β family belongs to a larger, extended super family of peptide signaling molecules that includes the Muellerian inhibiting substance (Cate, R. L. et al., *Cell,* 45:685–698 (1986)), decapentaplegic (Padgett, R. W. et al., *Nature* 325:81–84 (1987)), bone morphogenic factors (Wozney, J. M. et al., *Science* 242:1528–1534 (1988)), vg1 (Weeks, D. L., and Melton, D. A., *Cell* 51:861867 (1987)), activins (Vale, W. et al., *Nature,* 321:776–779 (1986)), and inhibins (Mason, A. J. et al., *Nature* 318:659–663 (1985)). These factors are similar to TGF-β in overall structure, but share only approximately 25% amino acid identity with the TGF-β proteins and with each other. All of these molecules are thought to play important roles in modulating growth, development and differentiation. TGF-β was originally described as a factor that induced normal rat kidney fibroblasts to proliferate in soft agar in the presence of epidermal growth factor (Roberts, A. B. et al., *Proc. Natl. Acad. Sci. USA* 78:5339–5343 (1981)). TGF-β has subsequently been shown to exert a number of different effects in a variety of cells. For example, TGF-β can inhibit the differentiation of certain cells of mesodermal origin (Florini, J. R. et al., *J. Biol. Chem.* 261:1659–16513 (1986)), induced the differentiation of others (Seyedine, S. M. et al., *Proc. Natl. Acad. Sci USA* 82:2267–2271 (1985)), and potently inhibit proliferation of various types of epithelial cells, (Tucker, R. F., *Science* 226:705–707 (1984)). This last activity has lead to the speculation that one important physiologic role for TGF-β is to maintain the repressed growth state of many types of cells. Accordingly, cells that lose the ability to respond to TGF-β are more likely to exhibit uncontrolled growth and to become tumorigenic. Indeed, the cells lack certain tumors such as retinoblastomas lack detectable TGF-β receptors at their cell surface and fail to respond to TGF-β, while their normal counterparts express self-surface receptors in their growth is potently inhibited by TGF-β (Kim Chi, A. et al., *Science* 240:196–198 (1988)). TGF-β1 has been shown to be a multi-functional regulator of cell growth and differentiation (Sporn et al., *Science* 233:532–534 (1986)) being capable of such diverse effects as inhibiting the growth of several human cancer cell lines, T and B lymphocytes (Kehrl et al., *J. Exp. Med.*

163:1037–1050 (1986)), inhibition of early hematopoietic progenitor cell proliferation (Goey et al., *J. Immunol.* 143:877–880 (1989)), stimulating the induction of differentiation of rat muscle mesenchymal cells and subsequent production of cartilage-specific macro molecules (Seyedine et. al., *J. Biol. Chem.* 262:1946–1949 (1986)), causing increased synthesis and secretion of collagen (Ignotz et al., *J. Biol. Chem.* 261:4337–4345 (1986)), stimulating bone formation (Noda et al., *Endocrinology*, 124:2991–2995 (1989)), and accelerating the healing of incision wounds (Mustoe et al., *Science* 237:1333–1335 (1987)). Further, TGF-β1 stimulates formation of extracellular matrix molecules in the liver and lung. When levels of TGF-β1 are higher than normal, formation of fiber occurs in the extracellular matrix of the liver and lung which can be fatal. High levels of TGF-β1 occur due to chemotherapy and bone marrow transplant as an attempt to treat cancers such as breast cancer. A second protein termed TGF-β2 has been isolated from several sources including demineralized bone, a human prostatic adenocarcinoma cell line (Ikeda et al., *Biol. Chem.* 26:2406–2410 (1987)). TGF-β2 shares several functional similarities with TGF-β1. These proteins are now known to be members of a family of related growth modulatory proteins including TGF-β3 (Ten-Dijke et al., *Proc. Natl. Acad. Sci. USA* 85:471–479 (1988)), Muellerian inhibitory substance and the inhibins.

Fibroblast growth factors (FGFs) represent another growing family of peptide growth factors with diverse activities (Miyamoto, M. et al., *Mol. and Cell. Biol.* 13(7):4251–4259 (1993)). These proteins share the characteristic of binding to heparin and are, therefore, also called heparin binding growth factors (HBGF). Expression of different members of the FGF family is found in various tissues under various temporal and spatial controls. These proteins are potent mitogens for a variety of cells of mesodermal, ectodermal, and endodermal origin, including fibroblasts, corneal and vascular endothelial cells, granulocytes, adrenal cortical cells, chondrocytes, myoblasts, vascular smooth muscle cells, lens epithelial cells, melanocytes, keratinocytes, oligodendrocytes, astrocytes, osteoblasts, and hematopoietic cells.

Each member of the FGF family has activities overlapping with others and also has its unique spectrum of functions (Burgess, W. H. and Maciag, T., *Ann. Rev. Biochem.* 58:575–606 (1989)). In addition to the ability to stimulate proliferation of vascular endothelial cells, both FGF-1 and 2 are chemotactic for endothelial cells, and FGF-2 has been shown to enable endothelial cells to penetrate the basement membrane. Consistent with these properties, both FGF-1 and 2 have the capacity to stimulate angiogenesis. Another important feature of these growth factors is their ability to promote wound healing. Many other members of the FGF family share similar activities with FGF-1 and 2 such as promoting angiogenesis and wound healing. Several members of the FGF family have been shown to induce mesoderm formation and to modulate differentiation of neuronal cells, adipocytes and skeletal muscle cells. Other than these biological activities in normal tissues, FGF proteins have been implicated in promoting tumorigenesis in carcinomas and sarcomas by promoting tumor vascularization and as transforming proteins when their expression is deregulated cells (Miyamoto, M., et al., *Mol. Cell. Biol.* 13(7):4251–4259 (1993)).

The formation of new blood vessels, or angiogenesis, is essential for embryonic development, subsequent growth, and tissue repair (Folkman, J. and Klagsbrun, M., *Science* 235:442–447(1987). Angiogenesis, however, is an essential part of certain pathological conditions such as neoplasia, for example, tumors and gliomas, and abnormal angiogenesis is associated with other diseases such as inflammation, rheumatoid arthritis, psoriasis, and diabetic retinopathy. Both acidic and basic fibroblast growth factor molecules are mitogens for endothelial cells and other cell types. Angiotropin and angiogenin can induce angiogenesis, although their functions are unclear. A highly selective mitogen for vascular endothelial cells is vascular endothelial growth factor or VEGF (Ferrara, N., et al., *Endocr. Rev.* 13:19–32, (1992)), also known as vascular permeability factor (VPF). Vascular endothelial growth factor is a secreted angiogenic mitogen whose target cell specificity appears to be restricted to vascular endothelial cells.

The murine VEGF gene has been characterized and its expression pattern in embryogenesis has been analyzed. A persistent expression of VEGF was observed in epithelial cells adjacent to fenestrated endothelium, e.g., in choroid plexus and kidney glomeruli. The data was consistent with a role of VEGF as a multifunctional regulator of endothelial cell growth and differentiation Breier, G. et al. *Development* 114:521–532 (1992)). VEGF is structurally related to the α and β chains of platelet-derived growth factor (PDGF), a mitogen for mesenchymal cells and placenta growth factor (PLGF), an endothelial cell mitogen. These three proteins belong to the same family and share a conserved motif. Eight cysteine residues contributing to disulfide-bond formation are strictly conserved in these proteins. Alternatively spliced mRNAs have been identified for both VEGF, PLGF and PDGF, and these different splicing products differ in biological activity and in receptor-binding specificity. VEGF and PDGF function as homodimers or heterodimers and bind to receptors which elicit intrinsic tyrosine kinase activity following receptor dimerization.

The temporal and spatial expression of VEGF has been correlated with physiological proliferation of the blood, and its high affinity binding sites are localized only on endothelial cells in tissue sections (Gajdusek, C. M., and Carbon, S. J., *Cell Physiol.* 139:570–579 (1989)); McNeil, P. L., Muthukrishnan, L., Warder, E., D'Amore, P. A., *J. Cell. Biol.* 109:811–822 (1989)). The factor can be isolated from pituitary cells and several tumor cell lines, and has been implicated in some human gliomas. Expression of some forms of VEGF confers on Chinese hamster ovary cells the ability to form tumors in nude mice (Ferrara, N., et al., *J. Clin. Invest.* 91:160–170 (1993)), and inhibition of VEGF function by anti-VEGF monoclonal antibodies was shown to inhibit tumor growth in immune-deficient mice (Kim, K. J., *Nature* 362:841–844 (1993)). Further, a dominant-negative mutant of the VEGF receptor has been shown to inhibit growth of glioblastomas in mice. Vascular permeability factor has also been found to be responsible for persistent microvascular hyperpermeability to plasma proteins even after the cessation of injury, which is a characteristic feature of normal wound healing. This suggests that VPF is an important factor in wound healing. Brown, L. F. et al., *J. Exp. Med.* 176:1375–9 (1992). The expression of VEGF is high in vascularized tissues (e.g., lung, heart, placenta and solid tumors) and correlates with angiogenesis both temporally and spatially. VEGF has also been shown to induce angiogenesis in vivo. Since angiogenesis is essential for the repair of normal tissues, especially vascular tissues, VEGF has been proposed for use in promoting vascular tissue repair (e.g., in atherosclerosis).

Thus, there is a need for polypeptides that function as growth factors in regulating a wide variety of developmental and physiological processes, since disturbances of such regulation may be involved in disorders relating to development, hemostasis, angiogenesis, tumor metastisis, cellular migration and ovulation, as well as neurogenesis. Therefore, there is a need for identification and characterization of new families of mammalian growth factors, particularly novel human growth factors, which can play a role in detecting, preventing, ameliorating or correcting such disorders.

Recently, insect homologs of several mammalian growth factors and their receptors have been genetically identified in Drosophila and suggested to play roles in oogenesis (Padgett, R. W. et al., *Nature* 325:81–84 (1987)); Fergoso, E. L. and Anderson, K. V., *Cell* 71:451–461 (1992); Stoehling-Hampton, K. et al., *Nature* 372:783–786 (1994); Panganiban, G. E. et al., *Mol. Cell Biol.* 10:2669–2677 (1990)), embryogenesis (Xia, T. et al., *Science* 283: 1756–1759 (1994); Raz, E. and Shilo, B. Z., *Genes & Dev.* 7: 1937–1943 (1993); Brand, A. H. and Perriman, N., *Genes & Dev.* 8: 629–639 (1994); Goode, S. et al., *Development* 116:177–192 (1992); Livneh, E. et al., *Cell* 40:599–607 (1985); Neuman-Silverberg, F. S. and Schupbach T., *Cell* 75:165–174 (1993)) and morphogenesis of specified organs (Heberlain, U. et al., *Cell* 75:913–926 (1993); Nellen, D. et al., *Cell* 78:225–237 (1994); Brummel, T. J. et al., *Cell* 78:251–261 (1994); Penton, A. et al., *Cell* 78:239–250 (1994)). For instance, a member of the Drosophila TGF-β family, decapentaplegic (dpp), was shown to act as a morphogen for dorsal-ventral pattern organization in Drosophila (Fergoso, E. L. and Anderson, K. V., supra).

However, a prototype for a new polypeptide growth factor family, for which no mammalian homolog was known, has recently been identified in insects (K. Homma et al., *J. Biochem.* 271:13370–13775 (1996)). This growth factor, termed "Insect-Derived Growth Factor (IDGF)," was isolated from the conditioned medium of NIH Sape-4 cells, an embryonic cell line of the flesh fly, and was purified to homogeneity. Like many other cell lines established from various insects, NIH Sape-4 cells inoculated at high density proliferated in the absence of fetal calf serum and known growth factors. As suggested by this finding, these embryonic insect cells were found to produce a growth factor, IDGF, that stimulates their proliferation in an autocrine manner. IDGF is a homodimer of a protein with a molecular mass of 52 kDa, and its specific activity for stimulating replication of cultured embryonic cells is comparable to those of mammalian growth factors in stimulating target cell replication. Imunoblotting experiments revealed that unfertilized mature eggs of the flesh fly contained this growth factor, a certain level of which was maintained throughout embryonic development. Analysis of cDNA for the growth factor showed that this factor is a novel protein consisting of 553 amino acids. No significant sequence similarity was found between this factor and other proteins except 25% amino acid identity shared with atrial gland granule-specific antigen (AGSA) of *Aplysia californica*, suggesting that this insect antigen for which no function was previously known is also a growth factor.

It is also known that dendritic cells (DC) are the principal antigen presenting cells involved in primary immune responses; their major function is to obtain antigen in tissues, migrate to lymphoid organs, and activate T cells (Mohamadzadeh, M. et al., *J. Immunol.* 156: 3102–3106 (1996). For example, Langerhans cells (LC), which are skin-specific members of this family, have been shown to present a variety of antigens that may be generated in or penetrate into skin. In contact hypersensitivity, topical application of a reactive hapten activates LC to migrate out of the epidermis into draining lymph nodes, where they present this antigen to selected T cells. Human LC lines secrete relatively large amounts of various chemokines such as NAP-1/IL-8 and MIP-1α upon ligation of CD40 on cell surfaces. Thus, it is likely that LC possess the potential to produce a selected set of chemokines with chemotactic activities for T cells.

DC are also the first immune cells to arrive at sites of inflammation on mucous membranes, the major site of sexual transmission of HIV. Weissman, D. et al., *J. Immunol.* 155:4111–4117 (1995) Mature DC in peripheral blood bind HIV to their surface and induce infection when added to autologous CD4+ T cells in the absence of added stimuli, such as mitogens. These mature DC, when isolated directly from peripheral blood, appear to be conjugated to T cells, and these conjugates are infected easily and productively with HIV. These findings suggest a role for DC in early HIV infection in which they bind virus and interact with T cells locally or after migrating to a lymphoid organ, thus establishing a productive infection. Furthermore, they likely play a role in the propagation of HIV infection by activating T cells in the presence of HIV, which leads to viral replication and immune cell destruction. Thus, there is a need for identifying new polypeptide factors which may mediate interactions between DC and T cells which may lead to T cell activation or HIV infection.

DiGeorge Syndrome, also called thymic aplasia (failure of organ to develop naturally), thymic hypoplasia (defective development of tissue), or third and fourth pharyngeal arch or pouch syndrome, is a congenital immune disorder characterized by lack of embryonic (stage in prenatal development between 2–8 weeks inclusive) development or underdevelopment of the pharyngeal pouches. The syndrome is often associated with congenital heart defects, anomalies of the great vessels, esophageal atresia (congenital failure of esophageal tube to develop) and abnormalities of facial structures, and low levels of serum calcium as a result of the hypoparathyroidism (insufficient secretion of the parathyroid glands). In most cases there is an observable chromosomal defect on chromosome 22.

Pathologically, DiGeorge Syndrome is characterized by absence or hypoplasia of the thymus and parathyroids with varying degrees of T cell immunodeficiency. Deficiency of cell-mediated immune response may result in increased susceptibility to infection. Depending on the degree of parathyroid or thymic hypoplasia, hypocalcemic tetany (intermittent, tonic spasms, paroxysmal and involving the extremities) may be present. DiGeorge Syndrome arises from a disturbance of normal embryologic development of the pharyngeal pouches between the sixth and 10th weeks of gestation. This disturbance can affect the first, second, third, fourth and sixth pharyngeal pouches, depending on when during this key time period the disturbance occurs. For example, a disturbance of the third and fourth pharyngeal pouches affects development of the thymus and aorta. Disturbances in the third pharyngeal pouch also affect development of the parathyroid, while disturbances in the first and second pharyngeal pouches affect lip and external ear development. Development of the pulmonary artery is influenced by the sixth pharyngeal pouch. Thus, to aid in the diagnosis and treatment of DiGeorge syndrome and similar pathologies, there is a need to identify polypeptide factors which map near the chromosome 22 locus associated with DiGeorge syndrome, are expressed early in development, and also have effects on embryonal cells.

SUMMARY OF THE INVENTION

The present invention provides isolated nucleic acid molecules comprising a polynucleotide encoding at least a portion of the DCDGF polypeptide having the complete amino acid sequence shown in FIG. 1 (SEQ ID NO:2) or the complete amino acid sequence encoded by the human cDNA clone deposited as plasmid DNA with the ATCC (Deposit Number 97852) on Jan. 17, 1997. The nucleotide sequence determined by sequencing the deposited DCDGF clone, which is shown in FIG. 1 (SEQ ID NO:1), contains an open reading frame encoding a complete polypeptide of 511 amino acid residues, including an initiation codon encoding an N-terminal methionine at nucleotide positions 1–3 in FIG. 1 (positions 74–78 of SEQ ID NO:1), and a predicted molecular weight of about 58.5 kDa. Nucleic acid molecules of the invention include those encoding the complete amino acid sequence excepting the N-terminal methionine shown in SEQ ID NO:2, or the complete amino acid sequence excepting the N-terminal methionine encoded by the human cDNA clone in ATCC Deposit Number 97852, which molecules also can encode additional amino acids fused to the N-terminus of the DCDGF amino acid sequence.

The DCDGF protein of the present invention shares sequence homology with the translation product of the insect *Sarcophaga perigrina* (flesh fly) mRNA for Insect-Derived Growth Factor (IDGF) (see FIG. 2; SEQ ID NO:3). Thus, the complete DCDGF amino acid sequence of SEQ ID NO:2 shares about 38.0% identity and about 58.2% similarity with the amino acid sequence encoded by the insect mRNA for IDGF (Homma et al., supra, which can be accessed on GenBank as Accession No. D83125), as determined by analysis with Bestfit (Wisconsin Sequence Analysis Package, Version 8 for Unix, Genetics Computer Group, University Research Park, 575 Science Drive, Madison, Wis. 53711) using the default parameters (see FIG. 2). The shared homology includes the conserved cysteines at positions 108 and 133 in SEQ ID NO:2, which also are conserved in the atrial gland granule-specific antigen (AGSA) of *Aplysia californica*, as reported by K. Homma et al., supra. IDGF is present throughout embryonic development and stimulates proliferation of embryonic insect cells and therefore is thought to be important in development of the insect from the fertilized egg. The homology between IDGF and DCDGF, as well as the facts that DCDGF is produced by dendritic cells, which activate T cells, and the gene for DCDGF has been mapped to a locus on chromosome 22 which is associated with DiGeorge Syndrome, all indicate involvement of DCDGF in early stages of human development and developmentally related pathologies including, for instance, DiGeorge Syndrome, as well as in immune system disorders, particularly relating to cellular immunity.

The encoded polypeptide has a predicted leader sequence of about the first 26 amino acids (underlined) in FIG. 1 (positions −26 to −1 in SEQ IN NO:2); and the amino acid sequence of the predicted mature DCDGF protein is shown as amino acid residues 1–485 in SEQ ID NO:2 (27 to 511 in FIG. 1). Thus, one aspect of the invention provides an isolated nucleic acid molecule comprising a polynucleotide comprising a nucleotide sequence selected from the group consisting of: (a) a nucleotide sequence encoding the full-length DCDGF polypeptide having the complete amino acid sequence in FIG. 1 (SEQ ID NO:2); (b) a nucleotide sequence encoding the DCDGF polypeptide having the complete amino acid sequence in FIG. 1 excepting the N-terminal methionine (i.e., residues −25 to +485 of SEQ ID NO:2); (c) a nucleotide sequence encoding the predicted mature DCDGF polypeptide having the amino acid sequence at positions 27 to 511 in FIG. 1 (i.e., residues 1 to 485 in SEQ ID NO:2); (d) a nucleotide sequence encoding the complete DCDGF polypeptide encoded by the human cDNA contained in ATCC Deposit No. 97852; (e) a nucleotide sequence encoding the DCDGF polypeptide having the complete amino acid sequence excepting the N-terminal methionine encoded by the human cDNA contained in ATCC Deposit No. 97852; (f) a nucleotide sequence encoding the mature DCDGF polypeptide having the amino acid sequence encoded by the human cDNA contained in ATCC Deposit No. 97852; and (g) a nucleotide sequence complementary to any of the nucleotide sequences in (a), (b), (c), (d), (e) or (f) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a DCDGF polypeptide having an amino acid sequence in (a), (b), (c), (d), (e) or (f), above.

The present invention also relates to recombinant vectors, which include the isolated nucleic acid molecules of the present invention, and to host cells containing the recombinant vectors, as well as to methods of making such vectors and host cells and for using them for production of DCDGF polypeptides or peptides by recombinant techniques.

The invention further provides an isolated DCDGF polypeptide comprising an amino acid sequence selected from the group consisting of: (a) the amino acid sequence of the full-length DCDGF polypeptide shown in FIG. 1 (SEQ ID NO:2); (b) the amino acid sequence of the full-length DCDGF polypeptide having the complete amino acid sequence shown in FIG. 1 excepting the N-terminal methionine (i.e., residues −25 to +485 of SEQ ID NO:2); (c) the amino acid sequence of the mature DCDGF polypeptide having the amino acid sequence at positions 27 to 511 (i.e., residues 1 to 485 in SEQ ID NO:2); (d) the amino acid sequence of the complete DCDGF polypeptide encoded by the human cDNA contained in ATCC Deposit No. 97852; (e) the amino acid sequence of the complete DCDGF polypeptide excepting the N-terminal methionine encoded by the human cDNA contained in ATCC Deposit No. 97852; and (f) the amino acid sequence of the mature DCDGF polypeptide encoded by the human cDNA contained in ATCC Deposit No. 97852. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) or (f) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a DCDGF polypeptide having an amino acid sequence described in (a), (b), (c), (d), (e) or (f), above. Peptides or polypeptides having the amino acid sequence of an epitope-bearing portion of a DCDGF polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a DCDGF polypeptide having an amino acid sequence described in (a), (b), (c), (d), (e) or (f) above. The invention further provides methods for isolating antibodies that bind specifically to a DCDGF polypeptide having an amino acid sequence as described herein. Such antibodies are useful diagnostically or therapeutically as described below.

The invention also provides pharmaceutical compositions comprising DCDGF polypeptides, particularly human DCDGF polypeptides, which may be employed, for instance, to treat immune system disorders, particularly relating to deficiencies in cellular immunity. Methods of treating individuals in need of DCDGF polypeptides to compensate for a deficiency in DCDGF or to enhance the normal level of DCDGF activity are also provided.

The invention further provides compositions comprising a DCDGF polynucleotide or an DCDGF polypeptide for administration to cells in vitro, to cells ex vivo and to cells in vivo, or to a multicellular organism. For instance, DCDGF polypeptides of the invention may be used to stimulate replication of various embryonic cells in culture, as a partial substitute for serum, for example, to produce cells for transplantation into a host needing such embryonic cells.

In certain particularly preferred embodiments of this aspect of the invention, the compositions comprise a DCDGF polynucleotide for expression of a DCDGF polypeptide in a host organism for treatment of disease. Particularly preferred in this regard is expression in a human patient for treatment of a dysfunction associated with aberrant endogenous activity of a DCDGF gene.

The present invention also provides a screening method for identifying compounds capable of enhancing or inhibiting a biological activity of the DCDGF polypeptide, which involves contacting a cell for which a cellular function such as replication is stimulated by a DCDGF polypeptide with the candidate compound in the presence of a DCDGF polypeptide, assaying cellular function stimulating activity of the DCDGF polypeptide in the presence of the candidate compound and of DCDGF polypeptide, and comparing the cellular function stimulating activity to a standard level of activity, the standard being assayed when contact is made between the cell and the DCDGF polypeptide in the absence of the candidate compound. In this assay, an increase in cellular function stimulation activity over the standard indicates that the candidate compound is an agonist of DCDGF activity and a decrease in cellular function stimulation activity compared to the standard indicates that the compound is an antagonist of DCDGF activity.

In another aspect, a screening assay for agonists and antagonists is provided which involves determining the effect a candidate compound has on DCDGF binding to a DCDGF receptor. In particular, the method involves contacting the DCDGF receptor with a DCDGF polypeptide and a candidate compound and determining whether DCDGF polypeptide binding to the DCDGF receptor is increased or decreased due to the presence of the candidate compound. In this assay, an increase in binding of DCDGF over the standard binding indicates that the candidate compound is an agonist of DCDGF binding activity and a decrease in DCDGF binding compared to the standard indicates that the compound is an antagonist of DCDGF binding activity.

It has been discovered that DCDGF mRNA is expressed not only in primary dendritic cells, from which the present prototype cDNA clone was isolated, but also in the following tissues at the approximate relative levels determined as indicated: by relative incidence of related cDNA clones in various libraries: activated monocytes (lower than dendritic cells), fetal heart, placenta, bone marrow, oxidized LDL-treated macrophages, Jurkats tumor, testes tumor, 8 week embryo (all lower than monocytes); and by Northern blotting: peripheral blood leukocytes (highest), lymph node, thymus and spleen (high), heart, pancreas, fetal liver and appendix (low but detectable). Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s).

In addition, for a number of disorders of the above tissues or cells, particularly functional disorders of the immune system and developmental disorders of the immune and other systems, especially DiGeorge Syndrome, significantly higher or lower levels of DCDGF gene expression may be detected in certain tissues (e.g., cancerous and wounded tissues) or bodily fluids (e.g., serum, plasma, urine, synovial fluid or spinal fluid) taken from an individual having such a disorder, relative to a "standard" DCDGF gene expression level, i.e., the DCDGF expression level in healthy tissue from an individual not having the immune or circulatory system disorder. Thus, the invention provides a diagnostic method useful during diagnosis of such a disorder, which involves: (a) assaying DCDGF gene expression level in cells or body fluid of an individual; (b) comparing the DCDGF gene expression level with a standard DCDGF gene expression level, whereby an increase or decrease in the assayed DCDGF gene expression level compared to the standard expression level is indicative of disorder in the immune system and/or a disorder related to early development, such as DiGeorge Syndrome.

More in particular, the DCDGF polynucleotides of the invention may be used for identifying chromosomal abnormalities indicative of DiGeorge Syndrome. For instance, as explained above, the range of symptoms associated with DiGeorge Syndrome depends on the severity of the developmental deficiency and the underlying genetic defect(s). Therefore, analysis of mutations in or near the DCDGF gene locus on chromosome 22 provides analytical data more precise than current chromosomal analyses for determining the prognosis for a fetus or infant suspected of suffering from DiGeorge Syndrome. Determination of which of the many abnormalities of the various types associated with DiGeorge Syndrome are related to DCDGF mutations also provides means for differential diagnosis and treatment of such abnormalities, which include cardiac and circulatory system defects, particularly of the aorta and pulmonary artery, parathyroid defects including hypocalcemia, various facial deformities, immune system deficiencies, particularly defects in cellular immunity.

An additional aspect of the invention is related to a method for treating an individual in need of an increased level of DCDGF activity in the body comprising administering to such an individual a composition comprising a therapeutically effective amount of an isolated DCDGF polypeptide of the invention or an agonist thereof. More in particular, DCDGF polypeptides and polynucleotides of the invention are useful in treating immune system defects due to dendritic cells failing to produce sufficient amounts of a DCDGF polypeptide or a sufficiently active form of a DCDGF polypeptide. In addition, the invention provides means for increasing the normal level of DCDGF T cell chemoattractant activity in a patient, for instance to enhance wound healing by applying DCDGF polypeptides to a wound or site of infection. More generally, DCDGF polypeptides and agonists can be used to stimulate replication of normal immune system cells in patients with immunodepressive conditions or various forms of leukemia or other immune system cancers, or who are undergoing chronic renal dialysis. Since some cancers are expected to involve autocrine stimulation of tumor cells by secretion of DCDGF polypeptide, DCDGF polypeptides and polynucleotides of the invention are useful for diagnosing such cancers.

A still further aspect of the invention is related to a method for treating an individual in need of a decreased level of DCDGF activity in the body comprising, administering to such an individual a composition comprising a therapeutically effective amount of a DCDGF antagonist. Preferred antagonists for use in the present invention are DCDGF-specific antibodies. Since some cancers are expected to involve autocrine stimulation of tumor cells by secretion of DCDGF polypeptide, antagonists of DCDGF activity are useful for treating them.

In addition, as noted above, dendritic cells (DC) are the first immune cells to arrive at sites of inflammation on mucous membranes, the major site of sexual transmission of HIV. Mature DC in peripheral blood bind HIV to their surface and induce infection when added to autologous CD4+ T cells in the absence of added stimuli, such as mitogens. These mature DC, when isolated directly from peripheral blood, appear to be conjugated to T cells, and these conjugates are infected easily and productively with HIV. These findings suggest a role for DC in early HIV infection in which they bind virus and interact with T cells locally or after migrating to a lymphoid organ, thus establishing a productive infection. Furthermore, they likely play a role in the propagation of HIV infection by activating T cells in the presence of HIV, which leads to viral replication and immune cell destruction. Accordingly, antagonists of DCDGF are useful for blocking interactions of DC with T cells mediated by DCDGF secreted from DC in early HIV infection, thereby preventing or slowing the establishment of a productive HIV infection.

BRIEF DESCRIPTION OF THE FIGURES

FIGS. 1A–C shows the nucleotide sequence (SEQ ID NO:1) and deduced amino acid sequence (SEQ ID NO:2) of DCDGF. The predicted leader sequence of about 26 amino acids is underlined. Note that the methionine residue at the beginning of the leader sequence is shown in FIG. 1 in position number (positive) 1, whereas the leader positions in the corresponding sequence of SEQ ID NO:2 are designated with negative position numbers. Thus, the leader sequence positions 1 to 26 in FIG. 1 correspond to positions −26 to −1 in SEQ ID NO:2. A predicted recognition sequence (RNV) for glycosylation on asparagine (N) is shown in italics at positions 126–128 of FIG. 1 (positions 100–102 of SEQ ID NO:2).

FIG. 2 shows the regions of identity between the amino acid sequences of the DCDGF protein (SEQ ID NO:2) and the translation product of the insect mRNA for IDGF (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

DETAILED DESCRIPTION

Figure 3:
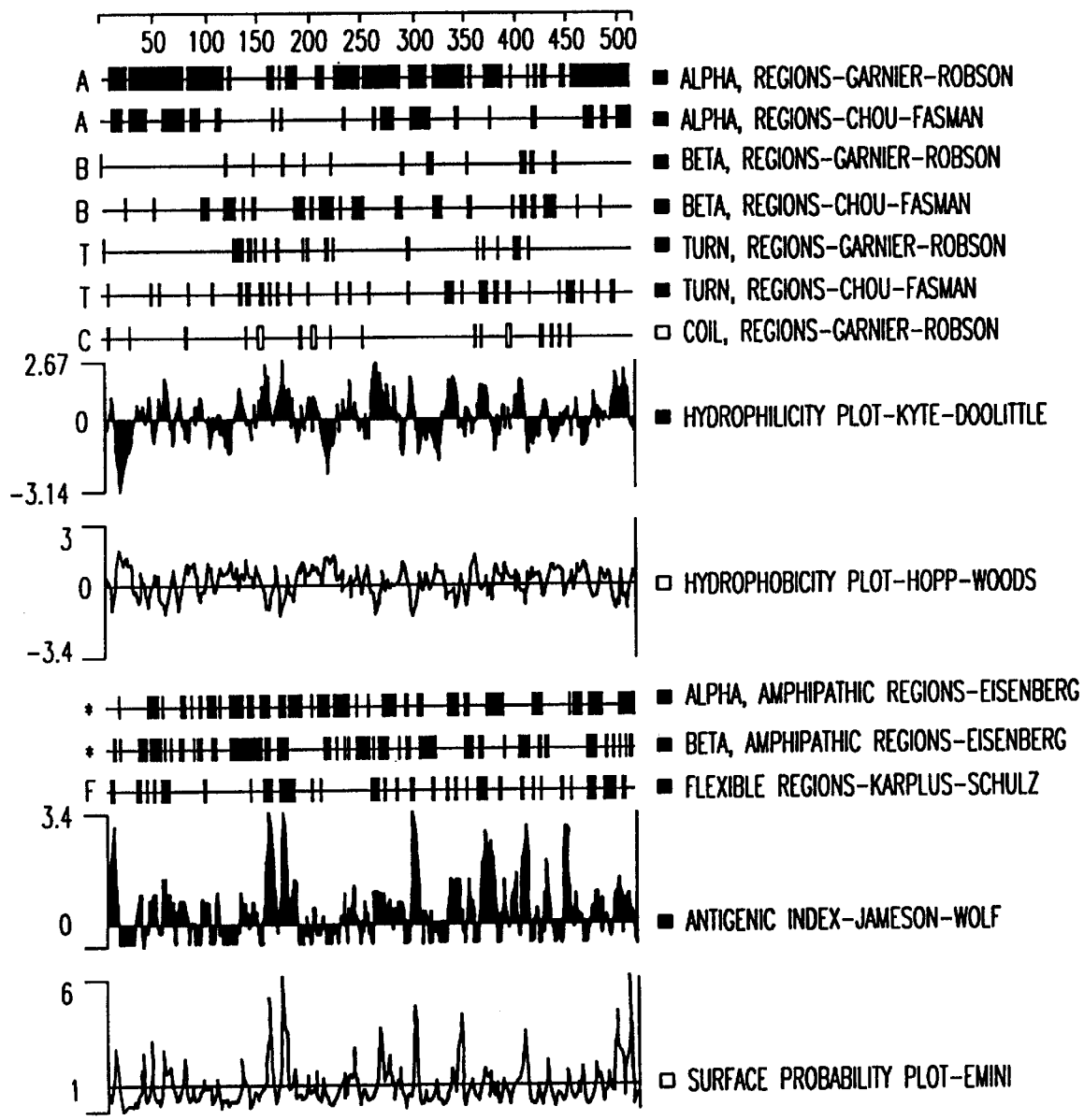
FIG. 3 shows an analysis of the DCDGF amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, the positive peaks indicate locations of the highly antigenic regions of the DCDGF protein, i.e., regions from which epitope-bearing peptides of the invention can be obtained.

The present invention provides isolated nucleic acid molecules comprising a polynucleotide encoding a DCDGF polypeptide having the amino acid sequence shown in SEQ ID NO:2, which was determined by sequencing a cloned cDNA. The nucleotide sequence shown in FIG. 1 (SEQ ID NO:1) was obtained by sequencing the HDPMJ44 cDNA clone, which was deposited on Jan. 17, 1997 at the American Type Culture Collection, Patent Depository, 10801 University Boulevard, Manassas, Va. 20110-2209, and given accession number ATCC 97852. The deposited clone is contained in the pCMVSport3.0 plasmid (Pharmacia, Gaithersburg, Md.).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIG. 1 (SEQ ID NO:1), a nucleic acid molecule of the present invention encoding a DCDGF polypeptide may be obtained using standard cloning and screening procedures, such as those for cloning cDNAs using mRNA as starting material. Illustrative of the invention, the nucleic acid molecule described in FIG. 1 (SEQ ID NO:1) was discovered in a cDNA library derived from primary dendritic cells. Additional clones of the same gene were also identified in cDNA libraries identified above.

The determined nucleotide sequence of the DCDGF cDNA of FIG. 1 (SEQ ID NO:1) contains an open reading frame encoding a protein of 511 amino acid residues.

As one of ordinary skill would appreciate, due to the possibilities of sequencing errors discussed above, the actual complete DCDGF polypeptide encoded by the deposited cDNA, which comprises about 511 amino acids, may be somewhat longer or shorter. Thus, the actual open reading frame may be anywhere in the range of 511±20 amino acids, more likely in the range of 511±10 amino acids, of that predicted from either the first methionine codon at the N-terminus shown in FIG. 1 (SEQ ID NO:1).

Leader and Mature Sequences

The amino acid sequence of the complete DCDGF protein includes a leader sequence and a mature protein, as shown in SEQ ID NO:2. More in particular, the present invention provides nucleic acid molecules encoding a mature form of the DCDGF protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide.

Therefore, the present invention provides a nucleotide sequence encoding the mature DCDGF polypeptide having the amino acid sequence encoded by the cDNA clone contained in the host identified as ATCC Deposit No. 97852. By the "mature DCDGF polypeptide having the amino acid sequence encoded by the cDNA clone in ATCC Deposit No. 97852" is meant the mature form(s) of the DCDGF protein produced by expression in a mammalian cell (e.g., COS cells, as described below) of the complete open reading frame encoded by the human DNA sequence of the clone contained in the vector in the deposited host.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues –13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete DCDGF polypeptide was analyzed by a computer program PSORT, available from Dr. Kenta Nakai of the Institute for Chemical Research, Kyoto University (see K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis of the DCDGF amino acid sequence by this program predicted a possible leader cleavage site before the Ser residue at position 22 of FIG. 1 (–5 of SEQ ID NO:2) which would yield a leader sequence of 21 amino acids. However, further analysis of the N-terminal sequence of DCDGF by visual inspection in light of known cleavage site sequences led to a prediction that the most probable site for cleavage of the leader is before the Ala residue at position 27 in FIG. 1 (position +1 of SEQ ID NO:2), yielding a leader of about 26 amino acids.

As one of ordinary skill would appreciate from the above discussions, due to the possibilities of sequencing errors as well as the variability of cleavage sites in different known proteins, the mature DCDGF polypeptide encoded by the deposited cDNA is expected to consist of about 485 amino acids (presumably residues 1 to 485 of SEQUENCE ID NO:2, but may consist of any number of amino acids in the range of about 476 to about 496 amino acids; and the actual leader sequence(s) of this protein is expected to consist of about 26 amino acids (presumably residues –26 through –1 of SEQ ID NO:2), but may consist of any number of amino acids in the range of about 16 to about 36 amino acids. More in particular, the invention provides DCDGF polypeptide fragments having a sequence shown in FIG. 1 which can be described as comprising residues 16 to 511, 17 to 511, 18 to 511, 19 to 511, 20 to 511, 21 to 511, 22 to 511, 23 to 511, 24 to 511, 25 to 511, 26 to 511, 27 to 511 28 to 511, 29 to 511, 30 to 511, 31 to 511, 32 to 511, 33 to 511, 34 to 511, 35 to 511, and 36 to 511.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 1–3 of the nucleotide sequence shown in FIG. 1 (SEQ ID NO:1). Also included are DNA molecules comprising the coding sequence for predicted mature DCDGF protein shown at positions 1–485 of SEQ ID NO:2. In addition, isolated nucleic acid molecules of the invention include DNA molecules which comprise a sequence substantially different from those described above but which, due to the degeneracy of the genetic code, still encode the DCDGF protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the DCDGF polypeptide having an amino acid sequence encoded by the cDNA clone contained in the plasmid deposited as ATCC Deposit No. 97852 on Jan. 17, 1997. Preferably, this nucleic acid molecule will encode the mature polypeptide encoded by the above-described deposited cDNA clone.

The invention further provides an isolated nucleic acid molecule having the nucleotide sequence shown in FIG. 1 (SEQ ID NO:1) or the nucleotide sequence of the DCDGF cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the DCDGF gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–1533 which encodes the open reading frame of SEQ ID NO:1.

In addition, the invention provides nucleic acid molecules having nucleotide sequences related to extensive portions of SEQ ID NO:1 which have been determined from the following related cDNA clones: HHFCU06 (sequence name HHFCU06R shown as SEQ ID NO:4), HHFFZ27 (sequence name HHFFZ27R shown as SEQ ID NO:5), HTTDS65 (sequence name HTTDS65R shown as SEQ ID NO:6) and HE8BJ92 (sequence name HE8BJ92R shown as SEQ ID NO:7). Further embodiments of the invention include isolated nucleic acid molecules that comprise a polynucleotide having a nucleotide sequence at least 90% identical, and more preferably at least 95%, 96%, 97%, 98% or 99% identical, to a polynucleotide comprising any portion of at least about 30 contiguous nucleotides, preferably at least about 50 contiguous nucleotides, of SEQ ID NO:1. Of the above nucleic acid molecules, preferrably excluded are those comprising a polynucleotide having a sequence of SEQ ID NO:4, SEQ ID NO:5, SEQ ID NO:6 or SEQ ID NO:7, or any fragment of at least 30, or preferably 50, contiguous nuceotides thereof.

More generally, by a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO:1). Preferred nucleic acid fragments of the present invention include nucleic acid molecules encoding epitope-bearing portions of the DCDGF polypeptide as identified in FIG. 3 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 97852. By "stringent hybridization conditions" is intended overnight incubation at 42° C. in a solution comprising: 50% formamide, 5×SSC 750 mM NaCl, 75 mM trisodium citrate, 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO:1)). Of course, a polynucleotide which hybridizes only to a poly A sequence (such as the 3' terminal poly(A) tract of the DCDGF cDNA), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a DCDGF polypeptide may include, but are not limited to those encoding the amino acid sequence of the mature polypeptide, by itself; and the coding sequence for the mature polypeptide and additional sequences, such as those encoding the about 26 amino acid leader or secretory sequence, such as a pre-, or pro- or prepro- protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the DCDGF fused to Fc at the N- or C-terminus.

Variant and Mutant Polynucleotides

The present invention further relates to variants of the nucleic acid molecules of the present invention, which encode portions, analogs or derivatives of the DCDGF protein. Variants may occur naturally, such as a natural allelic variant. By an "allelic variant" is intended one of several alternate forms of a gene occupying a given locus on a chromosome of an organism. *Genes II,* Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the DCDGF protein or portions thereof. Also especially preferred in this regard are conservative substitutions.

Most highly preferred are nucleic acid molecules encoding the mature protein having the amino acid sequence shown in SEQ ID NO:2 or the mature DCDGF amino acid sequence encoded by the deposited cDNA clone.

Further embodiments include an isolated nucleic acid molecule comprising a polynucleotide having a nucleotide sequence at least 90% identical, and more preferably at least 95%, 96%, 97%, 98% or 99% identical to a polynucleotide selected from the group consisting of: (a) a nucleotide sequence encoding the DCDGF polypeptide having the complete amino acid sequence shown in FIG. 1 (SEQ ID NO:2); (b) a nucleotide sequence encoding the DCDGF polypeptide having the complete amino acid sequence in FIG. 1 excepting the N-terminal methionine (i.e., positions −25 to +485 of SEQ ID NO:2); (c) a nucleotide sequence encoding the predicted mature DCDGF polypeptide having the amino acid sequence at positions 27 to 511 of FIG. 1 (1 to 485 of SEQ ID NO:2); (d) a nucleotide sequence encoding the DCDGF polypeptide having the complete amino acid seuqence encoded by the cDNA clone contained in ATCC Deposit No. 97852; (e) a nucleotide sequence encoding the DCDGF polypeptide having the complete amino acid sequence excepting the N-terminal methionine encoded by the cDNA clone contained in ATCC Deposit No. 97852; (f) a nucleotide sequence encoding the mature DCDGF polypeptide having the amino acid sequence encoded by the cDNA clone contained in ATCC Deposit No. 97852; and (f) a nucleotide sequence complementary to any of the nucleotide sequences in (a), (b), (c), (d), (e) or (f) above.

In a specific embodiment the invention encompasses an isolated nucleic acid molecule comprising a polynucleotide having a nucleotide sequence at least 95% identical to a sequence selected from the group consisting of: (a) a nucleotide sequence encoding a polypeptide comprising the amino acid sequence of residues n to 485 of SEQ ID NO:2, where n is any integer except zero in the range of about −25 to about +19; (b) a nucleotide sequence encoding a polypeptide comprising the amino acid sequence of residues −25 to m of SEQ ID NO:2, where m is any integer except zero in the range of 464 to 484; (c) a nucleotide sequence encoding a polypeptide having the amino acid sequence consisting of residues n to m of SEQ ID NO:2, where n and m are integers as defined respectively in (a) and (b) above; and (d) a nucleotide sequence encoding a polypeptide consisting of a portion of the complete DCDGF amino acid sequence encoded by the cDNA clone contained in ATCC Deposit No 97852 wherein said portion excludes from 1 to about 45 amino acids from the amino terminus of said complete amino acid sequence.

The present invention also relates to recombinant vectors, which include the isolated nucleic acid molecules of the present invention, and to host cells containing the recombinant vectors, as well as to methods of making such vectors and host cells and for using them for production of DCDGF polypeptides or peptides by recombinant techniques.

By a polynucleotide having a nucleotide sequence at least, for example, 95% "identical" to a reference nucleotide sequence encoding a DCDGF polypeptide is intended that the nucleotide sequence of the polynucleotide is identical to the reference sequence except that the polynucleotide sequence may include up to five point mutations per each 100 nucleotides of the reference nucleotide sequence encoding the DCDGF polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1) or to the nucleic acid sequence of the deposited cDNA, irrespective of whether they encode a polypeptide having DCDGF activity. This is because even where a particular nucleic acid molecule does not encode a polypeptide having DCDGF activity, one of skill in the art would still know how to use the nucleic acid molecule, for instance, as a hybridization probe or a polymerase chain reaction (PCR) primer. Uses of the nucleic acid molecules of the present invention that do not encode a polypeptide having DCDGF activity include, inter alia, (1) isolating the DCDGF gene or allelic variants thereof in a cDNA library; (2) in situ hybridization (e.g., "FISH") to metaphase chromosomal spreads to provide precise chromosomal location of the DCDGF gene, as described in Verma et al., Human Chromosomes: A Manual of Basic Techniques, Pergamon Press, New York (1988); and Northern Blot analysis for detecting DCDGF mRNA expression in specific tissues.

Preferred, however, are nucleic acid molecules having sequences at least 90%, 95%, 96%, 97%, 98% or 99% identical to the nucleic acid sequence shown in FIG. 1 (SEQ ID NO:1) or to the nucleic acid sequence of the deposited cDNA which do, in fact, encode a polypeptide having DCDGF protein activity. By "a polypeptide having DCDGF activity" is intended polypeptides exhibiting activity similar, but not necessarily identical, to an activity of the mature DCDGF protein of the invention, as measured in a particular biological assay. For example, the DCDGF protein of the present invention is expected to stimulate replication of embryonic cells in culture and have chemoattractant activity for T cells. In vitro assays for measuring the extent of stimulation of embryonal cell replication (e.g., as described for insect cells in Homma, et al., supra) or T cell chemoattraction are known in the art. Briefly, the assay for stimulation of embryonal cell involves seeding appropriate embryo cells in cultures under conditions (low cell density and no or low serum) where such cells do not replicate but remain viable, adding either (1) transfected host cell-supernatant containing DCDGF protein (or a candidate polypeptide) or (2) nontransfected host cell-supernatant control, and measuring the effect on embryonal cell replication by, for instance, cell counts or incorporation of labeled DNA precursor such as $^3$H-thymidine. Such activity is useful for determining relative levels of embryonic cell stimulatory activity of DCDGF polypeptides and candidate antagonists or agonists.

DCDGF stimulates embryonal cell replication and T cell chemoattraction in a dose-dependent manner in the above-described assay. Thus, "a polypeptide having DCDGF protein activity" includes polypeptides that also exhibit any of the same activities in the above-described assays in a dose-dependent manner. Although the degree of dose-dependent activity need not be identical to that of the DCDGF protein, preferably, "a polypeptide having DCDGF protein activity" will exhibit substantially similar dose-dependence in a given activity as compared to the DCDGF protein (i.e., the candidate polypeptide will exhibit greater activity or not more than about 25-fold less and, preferably, not more than about tenfold less activity relative to the reference DCDGF protein).

In addition DCDGF is expected to exhibit activity on leukocytes including for example monocytes, lymphocytes and neutrophils. For this reason DCDGF is active in directing the proliferation, differentiation and migration of these cell types. Such activity is useful for immune enhancement or suppression, myeloprotection, stem cell mobilization, acute and chronic inflammatory control and treatment of leukemia. Assays for measuring such activity are known in the art. For example, see Peters et al., *Immun. Today* 17:273 (1996); Young et al., *J. Exp. Med.* 182:1111 (1995); Caux et al., *Nature* 390:258 (1992); and Santiago-Schwarz et al., *Adv. Exp. Med. Biol.* 378:7 (1995).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having DCDGF protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having DCDGF protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of DCDGF polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods.

Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52–58 (1995) and K. Johanson et al., *J. Biol. Chem.* 270:9459–9471 (1995).

The DCDGF protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides an isolated DCDGF polypeptide having the amino acid sequence encoded by the deposited cDNA, or the amino acid sequence in SEQ ID NO:2, or a peptide or polypeptide comprising a portion of the above polypeptides.

Variant and Mutant Polypeptides

To improve or alter the characteristics of DCDGF polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. In the present case, since the protein of the invention is a member of the IDGF growth factor family in which the N-terminal region is not highly conserved, deletions of N-terminal amino acids up to the first two adjacent conserved residues (Leu and Gly at positions +20 and +21 in SEQ ID NO:2) may retain some biological activity such as receptor binding or modulation of target cell activities.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the DCDGF shown in SEQ ID NO:2, up to the Leu residue at position number 20, and polynucleotides encoding such polypeptides. In particular, the present invention provides polypeptides comprising the amino acid sequence of residues n-485 of SEQ ID NO:2, where n is any integer except zero in the range of –25 to +19. More in particular, the invention provides polynucleotides encoding polypeptides having the amino acid sequence of residues of –25 to 485, –24 to 485, –23 to 485, –22 to 485, –21 to 485, –20 to 485, –19 to 485, –18 to 485, –17 to 485, –16 to 485, –15 to 485, –14 to 485, –13 to 485, –12 to 485, –11 to 485, –10 to 485, –9 to 485, –8 to 485, –7 to 485, –6 to 485, –5 to 485, –4 to 485, –3 to 485, –2 to 485, –1 to 485, +1 to 485, +2 to 485, +3 to 485, +4 to 485, +5 to 485, +6 to 485, +7 to 485, +8 to 485, +9 to 485, +10 to 485, +11 to 485, +12 to 485, +13 to 485, +14 to 485, +15 to 485, +16 to 485, +17 to 485, +18 to 485 and +19 to 485 of SEQ ID NO:2. Polynucleotides encoding these polypeptides also are provided.

Similarly, many examples of biologically functional C-terminal deletion muteins are known. For instance interferon gamma shows up to ten times higher activities by deleting 8–10 amino acid residues from the carboxy terminus of the protein (Döbeli et al., *J. Biotechnology* 7:199–216 (1988). In the present case, deletions of up to about 20 C-terminal amino acids, to about the Lys at position 464 of SEQ ID NO:2, are expected to retain some biological activity such as receptor binding or modulation of target cell activities.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form of the protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the DCDGF shown in SEQ ID NO:2, up to Lys residue at position 464 of SEQ ID NO:2, and polynucleotides encoding such polypeptides. In particular, the present invention provides polypeptides comprising the amino acid sequence of residues −25 to m, preferrably −2 to m, of the amino acid sequence in SEQ ID NO:2, where m is any integer in the range of 464 to 484. More in particular, the invention provides polynucleotides encoding polypeptides having the amino acid sequence of residues −25 to +464, −25 to +465, −25 to +466, −25 to +467, −25 to +468, −25 to +469, −25 to +470, −25 to +471, −25 to +472, −25 to +473, −25 to +474, −25 to +475, −25 to +476, −25 to +477, −25 to +478, −25 to +479, −25 to +480, −25 to +481, −25 to +482 and -25 to +484 of SEQ ID NO:2. Polynucleotides encoding these polypeptides also are provided.

The invention also provides polypeptides having one or more amino acids deleted from both the amino and the carboxyl termini, which may be described generally as having residues at positions n-m of SEQ ID NO:2, where n and m are integers as described above.

Also included are a nucleotide sequence encoding a polypeptide consisting of a portion of the complete DCDGF amino acid sequence encoded by the cDNA clone contained in ATCC Deposit No. 97852, where this portion excludes from 1 to about 45 amino acids from the amino terminus of the complete amino acid sequence encoded by the cDNA clone contained in ATCC Deposit No. 97852, or from 1 to about 20 amino acids from the carboxy terminus, or any combination of the above amino terminal and carboxy terminal deletions, of the complete amino acid sequence encoded by the cDNA clone contained in ATCC Deposit No. 97852. Polynucleotides encoding all of the above deletion mutant polypeptide forms also are provided.

Other Mutants

In addition to terminal deletion forms of the protein discussed above, it also will be recognized by one of ordinary skill in the art that some amino acid sequences of the DCDGF polypeptide can be varied without significant effect of the structure or function of the protein. If such differences in sequence are contemplated, it should be remembered that there will be critical areas on the protein which determine activity.

Thus, the invention further includes variations of the DCDGF polypeptide which show substantial DCDGF polypeptide activity or which include regions of DCDGF protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the DCDGF of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |

TABLE 1-continued

Conservative Amino Acid Substitutions.

| | |
|---|---|
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the DCDGF protein of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).

Replacement of amino acids can also change the selectivity of the binding of a ligand to cell surface receptors. For example, Ostade et al., Nature 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al. Science 255:306–312 (1992)).

The polypeptides of the present invention are preferably provided in an isolated form, and preferably are substantially purified. A recombinantly produced version of the DCDGF polypeptide can be substantially purified by the one-step method described in Smith and Johnson, Gene 67:31–40 (1988). Polypeptides of the invention also can be purified from natural or recombinant sources using anti-DCDGF antibodies of the invention in methods which are well known in the art of protein purification.

The invention further provides an isolated DCDGF polypeptide comprising an amino acid sequence selected from the group consisting of: (a) the amino acid sequence of the full-length DCDGF polypeptide having the complete amino acid sequence shown in FIG. 1 (SEQ ID NO:2); (b) the amino acid sequence of the full-length DCDGF polypeptide having the complete amino acid sequence shown in FIG. 1 excepting the N-terminal methionine (i.e., positions −25 to +485 of SEQ ID NO:2); (c) the amino acid sequence of the mature DCDGF polypeptide having the amino acid sequence at positions 1 to 485 in SEQ ID NO:2; (d) the amino acid sequence of the full-length polypeptide encoded by the human cDNA contained in ATCC Deposit No. 97852; (e) the amino acid sequence of the complete DCDGF polypeptide excepting the N-terminal methionine encoded by the human cDNA contained in ATCC Deposit No. 97852; and (f) the amino acid sequence of the mature DCDGF polypeptide encoded by the human cDNA contained in ATCC Deposit No. 97852. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) or (f) above, and also include portions of such polypeptides with at least 30 amino acids and more preferably at least 50 amino acids.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a DCDGF polypeptide is intended that the amino acid sequence of the polypeptide is identical to the reference sequence except that the polypeptide sequence may include up to five amino acid alterations per each 100 amino acids of the reference amino acid of the DCDGF polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting DCDGF protein expression as described below or as agonists and antagonists capable of enhancing or inhibiting DCDGF protein function. Further, such polypeptides can be used in the yeast two-hybrid system to "capture" DCDGF protein binding proteins which are also candidate agonists and antagonists according to the present invention. The yeast two hybrid system is described in Fields and Song, *Nature* 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," *Science,* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate DCDGF-specific antibodies include: a polypeptide comprising amino acid residues from about Leu at position −25 to about Ala at position −16 of SEQ ID NO:2, a polypeptide comprising amino acid residues from about His 124 to about Lys 135 of SEQ ID NO:2, a polypeptide comprising amino acid residues from about Leu 139 to about Val 149 of SEQ ID NO:2, a polypeptide comprising amino acid residues from about Gly 332 to about Leu 346 of SEQ ID NO:2, a polypeptide comprising amino acid residues from about Tyr 371 to about Ile 379 of SEQ ID NO:2, and a polypeptide comprising amino acid residues from about Ile 412 to about Met 419 of SEQ ID NO:2. These polypeptide fragments have been determined to bear antigenic epitopes of the DCDGF protein by the analysis of the Jameson-Wolf antigenic index, as shown in FIG. 3, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, DCDGF polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., *Nature* 331:84–86 (1988)). Fusion proteins that have a disulfide4inked dimeric structure due to the IgG part can also be more efficient in binding and neutralizing other molecules than the monomeric DCDGF protein or protein fragment alone (Fountoulakis et al., *J. Biochem.* 270:3958–3964 (1995)).

Antibodies

DCDGF-protein specific antibodies for use in the present invention can be raised against the intact DCDGF protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to DCDGF protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the DCDGF protein or an antigenic fragment thereof can be administered to an animal in order to induce the production of sera containing polyclonal antibodies. In a preferred method, a preparation of DCDGF protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or DCDGF protein binding fragments thereof). Such monoclonal antibodies can be prepared using hybridoma technology (Köhler et al., *Nature* 256:495 (1975); Köhler et al., *Eur. J. Immunol.* 6:511 (1976); Köhler et al., *Eur. J. Immunol.* 6:292 (1976); Hammerling et al., in: *Monoclonal Antibodies and T-Cell Hybridomas,* Elsevier, N.Y., (1981) pp. 563–681 ). In general, such procedures involve immunizing an animal (preferably a mouse) with a DCDGF protein antigen or, more preferably, with a DCDGF protein-expressing cell. Suitable cells can be recognized by their capacity to bind anti-DCDGF protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the American Type Culture Collection, Rockville, Md. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the DCDGF protein antigen.

Alternatively, additional antibodies capable of binding to the DCDGF protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, DCDGF-protein specific antibodies are used to immunize an animal, preferably a mouse. The splenocytes of such an animal are then used to produce hybridoma cells, and the hybridoma cells are screened to identify clones which produce an antibody whose ability to bind to the DCDGF protein-specific antibody can be blocked by the DCDGF protein antigen. Such antibodies comprise anti-idiotypic antibodies to the DCDGF protein-specific antibody and can be used to immunize an animal to induce formation of further DCDGF protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, DCDGF protein-binding fragments can be produced through the application of recombinant DNA technology or through synthetic chemistry.

For in vivo use of anti-DCDGF in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Immune System and Developmentally-Related Disorders

Diagnosis

The present inventors have discovered that DCDGF mRNA is expressed not only in primary dendritic cells, from which the present prototype cDNA clone was isolated, but also in the following tissues at the approximate relative levels determined as indicated: by relative incidence of related cDNA clones in various libraries: activated monocytes (lower than dendritic cells), fetal heart, placenta, bone marrow, oxidized LDL-treated macrophages, Jurkats tumor, testes tumor, 8 week embryo (all lower than monocytes); and by Northern blotting: peripheral blood leukocytes (highest), lymph node, thymus and spleen (high), heart, pancreas, fetal liver and appendix (low but detectable). Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s).

In addition, for a number of disorders of the above tissues or cells, particularly functional disorders of the immune system and developmental disorders of the immune and other systems, especially DiGeorge Syndrome, significantly higher or lower levels of DCDGF gene expression may be detected in certain tissues (e.g., cancerous and wounded tissues) or bodily fluids (e.g., serum, plasma, urine, synovial fluid or spinal fluid) taken from an individual having such a disorder, relative to a "standard" DCDGF gene expression level, i.e., the DCDGF expression level in healthy tissue from an individual not having the immune or circulatory system disorder. Thus, the invention provides a diagnostic method useful during diagnosis of such a disorder, which involves: (a) assaying DCDGF gene expression level in cells or body fluid of an individual; (b) comparing the DCDGF gene expression level with a standard DCDGF gene expression level, whereby an increase or decrease in the assayed DCDGF gene expression level compared to the standard expression level is indicative of disorder in the immune system and/or a disorder related to early development, such as DiGeorge Syndrome.

In particular, it is believed that certain tissues in mammals with cancer, especially cancers of cells in the immune system, express significantly enhanced levels of the DCDGF protein and mRNA encoding the DCDGF protein when compared to a corresponding "standard" level. Further, it is believed that enhanced levels of the DCDGF protein can be detected in certain body fluids (e.g., sera, plasma, urine, and spinal fluid) from mammals with such a cancer when compared to sera from mammals of the same species not having the cancer. Thus, the invention provides a diagnostic method useful during diagnosis of an immune system disorder, which involves measuring the expression level of the gene encoding the DCDGF protein in immune system tissue or other cells or body fluid from an individual and comparing the measured gene expression level with a standard DCDGF gene expression level, whereby an increase or decrease in the gene expression level compared to the standard is indicative of immune system disorder. Where a diagnosis of a disorder in the immune, including diagnosis of a cancerous condition such as leukemia, has already been made according to conventional methods, the present invention is useful as a prognostic indicator, whereby patients exhibiting enhanced DCDGF gene expression will experience a worse clinical outcome relative to patients expressing the gene at a level nearer the standard level.

By "assaying the expression level of the gene encoding the DCDGF protein" is intended qualitatively or quantitatively measuring or estimating the level of the DCDGF protein or the level of the mRNA encoding the DCDGF protein in a first biological sample either directly (e.g., by determining or estimating absolute protein level or mRNA level) or relatively (e.g., by comparing to the DCDGF protein level or mRNA level in a second biological sample). Preferably, the DCDGF protein level or mRNA level in the first biological sample is measured or estimated and compared to a standard DCDGF protein level or mRNA level, the standard being taken from a second biological sample obtained from an individual not having the disorder or being determined by averaging levels from a population of individuals not having a disorder of the immune system. As will be appreciated in the art, once a standard DCDGF protein level or mRNA level is known, it can be used repeatedly as a standard for comparison.

By "biological sample" is intended any biological sample obtained from an individual, body fluid, cell line, tissue culture, or other source which contains DCDGF protein or mRNA. As indicated, biological samples include body fluids (such as sera, plasma, urine, synovial fluid and spinal fluid) which contain free DCDGF protein, immune system tissue, and other tissue sources found to express complete or mature DCDGF or a DCDGF receptor. Methods for obtaining tissue biopsies and body fluids from mammals are well known in the art. Where the biological sample is to include mRNA, a tissue biopsy is the preferred source.

The present invention is useful for diagnosis or treatment of various immune system-related disorders in mammals, preferably humans. Such disorders include and any disregulation of immune cell function including, but not limited to, autoimmunity, arthritis, leukemias, lymphomas, immunosuppression, immunity, humoral immunity, inflammatory bowel disease, myelo suppression and the like.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the DCDGF protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying DCDGF protein levels in a biological sample can occur using antibody-based techniques. For example, DCDGF protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting DCDGF protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying DCDGF protein levels in a biological sample obtained from an individual, DCDGF protein can also be detected in vivo by imaging. Antibody labels or markers for in vivo imaging of DCDGF protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A DCDGF protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain DCDGF protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

As noted above, DCDGF polynucleotides and polypeptides are useful for diagnosis of conditions involving abnormally high or low expression of DCDGF activities. Given the cells and tissues where DCDGF is expressed as well as the activities modulated by DCDGF, it is readily apparent that a substantially altered (increased or decreased) level of expression of DCDGF in an individual compared to the standard or "normal" level produces pathological conditions related to the bodily system(s) in which DCDGF is expressed and/or is active.

It will also be appreciated by one of ordinary skill that, since the DCDGF protein of the invention is a member of the IDGF family, which is a secreted polypeptide growth factor, the mature DCDGF protein may be released in soluble form from the cells which express the DCDGF by proteolytic cleavage. Therefore, when DCDGF mature form is added from an exogenous source to cells, tissues or the body of an individual, the protein will exert its physiological activities on its target cells of that individual.

Therefore, it will be appreciated that conditions caused by a decrease in the standard or normal level of DCDGF activity in an individual, particularly disorders of the immune system, can be treated by administration of DCDGF polypeptide (particularly in the form of the mature polypeptide or a mutant thereof). Thus, the invention also provides a method of treatment of an individual in need of an increased level of DCDGF activity comprising administering to such an individual a pharmaceutical composition comprising an amount of an isolated DCDGF polypeptide of the invention, particularly a mature form of the DCDGF protein of the invention, effective to increase the DCDGF activity level in such an individual.

Formulations

The DCDGF polypeptide composition will be formulated and dosed in a fashion consistent with good medical practice, taking into account the clinical condition of the individual patient (especially the side effects of treatment with DCDGF polypeptide alone), the site of delivery of the DCDGF polypeptide composition, the method of administration, the scheduling of administration, and other factors known to practitioners. The "effective amount" of DCDGF polypeptide for purposes herein is thus determined by such considerations.

As a general proposition, the total pharmaceutically effective amount of DCDGF polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the DCDGF polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the DCDGF of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The DCDGF polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release DCDGF polypeptide compositions also include liposomally entrapped DCDGF polypeptide. Liposomes containing DCDGF polypeptide are prepared by methods known per se: DE 3,218,121; Epstein et al., *Proc. Natl. Acad. Sci. (USA)* 82:3688–3692 (1985); Hwang et al., *Proc. Natl. Acad. Sci. (USA)* 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal DCDGF polypeptide therapy.

For parenteral administration, in one embodiment, the DCDGF polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the DCDGF polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The DCDGF polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of DCDGF polypeptide salts.

DCDGF polypeptide to be used for therapeutic administration must be sterile. Sterility is readily accomplished by filtration through sterile filtration membranes (e.g., 0.2 micron membranes). Therapeutic DCDGF polypeptide compositions generally are placed into a container having a sterile access port, for example, an intravenous solution bag or vial having a stopper pierceable by a hypodermic injection needle.

DCDGF polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous DCDGF polypeptide solution, and the resulting mixture is lyophilized. The infusion solution is prepared by reconstituting the lyophilized DCDGF polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of DCDGF on cells, such as its interaction with DCDGF-binding molecules such as receptor molecules. An agonist is a compound which increases the natural biological functions of DCDGF or which functions in a manner similar to DCDGF, while antagonists decrease or eliminate such functions.

In another aspect of this embodiment the invention provides a method for identifying a receptor protein or other ligand-binding protein which binds specifically to a DCDGF polypeptide. For example, a cellular compartment, such as a membrane or a preparation thereof, may be prepared from a cell that expresses a molecule that binds DCDGF. The preparation is incubated with labeled DCDGF and complexes of DCDGF bound to the receptor or other binding protein are isolated and characterized according to routine methods known in the art. Alternatively, the DCDGF polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds DCDGF, such as a molecule of a signaling or regulatory pathway modulated by DCDGF. The preparation is incubated with labeled DCDGF in the absence or the presence of a candidate molecule which may be a DCDGF agonist or antagonist. The ability of the candidate molecule to bind the binding molecule is reflected in decreased binding of the labeled ligand. Molecules which bind gratuitously, i.e., without inducing the effects of DCDGF on binding the DCDGF binding molecule, are most likely to be good antagonists. Molecules that bind well and elicit effects that are the same as or closely related to DCDGF are agonists.

DCDGF-like effects of potential agonists and antagonists may by measured, for instance, by determining activity of a second messenger system following interaction of the candidate molecule with a cell or appropriate cell preparation, and comparing the effect with that of DCDGF or molecules that elicit the same effects as DCDGF. Second messenger systems that may be useful in this regard include but are not limited to AMP guanylate cyclase, ion channel or phosphoinositide hydrolysis second messenger systems.

Another example of an assay for DCDGF antagonists is a competitive assay that combines DCDGF and a potential antagonist with membrane-bound DCDGF receptor molecules or recombinant DCDGF receptor molecules under appropriate conditions for a competitive inhibition assay. DCDGF can be labeled, such as by radioactivity, such that the number of DCDGF molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing DCDGF-induced activities, thereby preventing the action of DCDGF by excluding DCDGF from binding.

Other potential antagonists include antisense molecules. Antisense technology can be used to control gene expression through antisense DNA or RNA or through triple-helix formation. Antisense techniques are discussed, for example, in Okano, *J. Neurochem.* 56: 560 (1991); "Oligodeoxynucleotides as Antisense Inhibitors of Gene Expression." CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of DCDGF. The antisense RNA oligonucleotide hybridizes to the mRNA in vivo and blocks translation of the mRNA molecule into DCDGF polypeptide. The oligonucleotides described above can also be delivered to cells such that the antisense RNA or DNA may be expressed in vivo to inhibit production of DCDGF protein. The agonists and antagonists may be employed in a composition with a pharmaceutically acceptable carrier, e.g., as described above.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a DCDGF protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man,* available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

In the present case, the human DCDGF gene has been mapped as described above to the 22q1 locus on chromosome 22. This locus is associated with DiGeorge Syndrome which includes a wide variety of developmentally based defects as described hereinabove. Chromosomal breaks points related to leukemias also have been reported at this locus.

Having generally described the invention, the same will be more readily understood by reference to the following examples, which are provided by way of illustration and are not intended as limiting.

EXAMPLES

Example 1(a)

Expression and Purification of "His-tagged" DCDGF in *E. coli*

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6 X His tag") covalently linked to the amino terminus of that polypeptide.

The DNA sequence encoding the desired portion of the DCDGF protein comprising the mature of the DCDGF amino acid sequence is amplified from the deposited cDNA clone using PCR oligonucleotide primers which anneal to the amino terminal sequences of the desired portion of the DCDGF protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature form of the DCDGF protein, the 5' primer has the sequence 5' CAT GGATCCAGCTCTATCCATAGATGAAACACG 3' (SEQ ID NO:8) containing the underlined BamHI restriction site followed by 18 nucleotides of the amino terminal coding sequence of the mature DCDGF sequence in SEQ ID NO:2. One of ordinary skill in the art would appreciate, of course, that the point in the protein coding sequence where the 5' primer begins may be varied to amplify a DNA segment encoding any desired portion of the complete DCDGF protein shorter or longer than the mature form of the protein.

The 3' primer has the sequence 5'-GCA AAGCTTGGCTAGCTTCTCCTCACTTTG 3' (SEQ ID NO:9) containing the underlined HindIII restriction site followed by 13 nucleotides complementary to sequences 3' to end of the coding sequence of the DNA sequence in FIG. 1, a stop codon and the last 5 nucleotides of the coding sequence. The amplified DCDGF DNA fragment and the vector pQE9 are digested with BamHI and HindIII and the digested DNAs are then ligated together. Insertion of the DCDGF DNA into the restricted pQE9 vector places the DCDGF protein coding region downstream from the IPTG-inducible promoter and in-frame with an initiating AUG and the six histidine codons.

The ligation mixture is transformed into competent *E. coli* cells using standard procedures such as those described in Sambrook et al., *Molecular Cloning: a Laboratory Manual,* 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing DCDGF protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 $\mu$g/ml) and kanamycin (25 $\mu$g/ml). The ON culture is used to inoculate a large culture, at a dilution of approximately 1:25 to 1:250. The cells are grown to an optical density at 600 nm ("OD600") of between 0.4 and 0.6. Isopropyl-$\beta$-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the DCDGF is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the DCDGF is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80 C.

The following alternative method may be used to purify DCDGF expressed in *E. coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the DCDGF polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded DCDGF polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the DCDGF polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2

Cloning and Expression of DCDGFprotein in a Baculovirus Expression System

In this illustrative example, the plasmid shuttle vector pA2 is used to insert the cloned DNA encoding complete protein, including its naturally associated secretory signal (leader) sequence, into a baculovirus to express the mature baculovirus protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the full length DCDGF protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' CTA <u>GGATCC</u>GCCATCATGTTGGTGGATGGCCCATCTG-3': (SEQ ID NO:10) containing the underlined BamHI restriction enzyme site, an efficient signal for initiation of translation in eukaryotic cells, as described by Kozak, M.,*J. Mol. Biol.* 196:947–950 (1987), followed by 22 of nucleotides of the sequence of the complete DCDGF protein shown in FIG. 1, beginning with the AUG initiation codon. The 3' primer has the sequence 5' GCA <u>TCTAGA</u>GGCTAGCTTCTCCTCACTTTG-3' (SEQ ID NO:11) containing the underlined XbaI restriction site followed by 13 nucleotides complementary to sequences in the deposited clone 3' to the end of the coding sequence of the DNA sequence in FIG. 1, a stop codon and the last 5 nucleotides of the coding sequence. The amplified fragment is isolated from a 1% agarose gel using a commercially available kit ("Geneclean," BIO 101 Inc., La Jolla, Calif.). The fragment then is digested with BamHI and XbaI and again is purified on a 1% agarose gel. This fragment is designated herein F1.

The plasmid is digested with the restriction enzymes BamHI and XbaI and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB 101 or other suitable E. coli hosts such as XL-1 Blue (Statagene Cloning Systems, La Jolla, Calif.) cells are transformed with the ligation mixture and spread on culture plates. Bacteria are identified that contain the plasmid with the human DCDGF gene by digesting DNA from individual colonies BamHI and XbaI and then analyzing the digestion product by gel electrophoresis. The sequence of the cloned fragment is confirmed by DNA sequencing. This plasmid is designated herein pA2DCDGF.

Five µg of the plasmid pA2DCDGF is co-transfected with 1.0 µg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413–7417 (1987). One µg of BaculoGold™ virus DNA and 5 µg of the plasmid pA2DCDGF are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-DCDGF.

To verify the expression of the DCDGF gene, Sf9 cells are grown in Grace's medium supplemented with 10% heat-inactivated FBS. The cells are infected with the recombinant baculovirus V-DCDGF at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the DCDGF protein and thus the cleavage point and length of the naturally associated secretory signal peptide.

Example 3

Cloning and Expression of DCDGF in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CVI, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pDCDGF HA, is made by cloning a portion of the cDNA encoding the mature of the DCDGF protein into the expression vector pcDNAI/Amp or pcDNAIII (which can be obtained from Invitrogen, Inc.). The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the complete DCDGF polypeptide is cloned into the polylinker region of the vector so that recombinant protein expression is directed by the CMV promoter. The plasmid construction strategy is as follows. The DCDGF cDNA of the deposited clone is amplified using primers that contain convenient restriction sites, much as described above for construction of vectors for expression of DCDGF in *E. coli*. Suitable primers include the following, which are used in this example. The 5' primer, containing the underlined BamHI site, a Kozak sequence, followed by 22 of nucleotides of the sequence of the complete DCDGF protein shown in FIG. 1, beginning with the AUG initiation codon, has the following sequence: 5' CTA GGATCCGCCATCATGTTGGTGGATGGCCCATCTG-3': (SEQ ID NO:10) The 3' primer, containing the underlined XbaI site followed by 13 nucleotides complementary to sequences in the deposited clone 3' to the end of the coding sequence of the DNA sequence in FIG. 1, a stop codon and the last 5 nucleotides of the coding, has the following sequence: 5' GCA TCTAGAGGCTAGCTTCTCCTCACTTTG-3' (SEQ ID NO:11).

The PCR amplified DNA fragment and the vector, pcDNAI/Amp, are digested with BamHI and XbaI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the complete polypeptide For expression of recombinant DCDGF, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, New York (1989). Cells are incubated under conditions for expression of DCDGF by the vector.

Expression of the DCDGF-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, New York (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of polypeptide. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the DCDGF polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction BamHI and XbaI and then dephosphorylated using calf intestinal phosphates by procedures known in the art. The vector is then isolated from a 1% agarose gel. The DNA sequence encoding the complete polypeptide is amplified using PCR oligonucleotide primers corresponding to the 5' and 3' sequences of the desired portion of the gene. The 5' primer containing the underlined site containing the underlined BamHI site, a Kozak sequence, followed by 22 of nucleotides of the sequence of the complete DCDGF protein shown in FIG. 1, beginning with the AUG initiation codon, has the following sequence: 5' CTA GGATCCGCCATCATGTTGGTGGATGGCCCATCTG-3': (SEQ ID NO:10). The 3' primer, containing the underlined XbaI site followed by 13 nucleotides complementary to sequences in the deposited clone 3' to the end of the coding sequence of the DNA sequence in FIG. 1, a stop codon and the last 5 nucleotides of the coding, has the following sequence: 5' GCA TCTAGAGGCTAGCTTCTCCTCACTTTG-3' (SEQ ID NO:11).

The amplified fragment is digested with the endonucleases BamHI and XbaI and then purified again on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 M, 5 μM, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Tissue distribution of DCDGF mRNA expression

Northern blot analysis is carried out to examine DCDGF gene expression in human tissues, using methods described by, among others, Sambrook et al., cited above. A cDNA probe containing the entire nucleotide sequence of the DCDGF protein (SEQ ID NO:1) is labeled with $^{32}$P using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for DCDGF mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT 1190-1. Following hybridization and washing, the blots are mounted and exposed to film at −70° C. overnight, and films developed according to standard procedures.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule comprising a first polynucleotide sequence 95% or more identical to a second polynucleotide sequence selected from the group consisting of:

(a) a polynucleotide sequence encoding amino acids −26 to 485 of SEQ ID NO:2;

(b) a polynucleotide sequence encoding amino acids −25 to 485 of SEQ ID NO:2;

(c) a polynucleotide sequence encoding amino acids 1 to 485 of SEQ ID NO:2; and (d) a polynucleotide sequence complementary to any of the polynucleotide sequences in (a), (b) or (c) above;

wherein percentage identity is determined using the BESTFIT program with parameters that calculate identity over the full length of the second polynucleotide sequence and that allows gaps of up to 5% of the total number of nucleotides of said nucleotide sequence.

2. The isolated nucleic acid molecule of claim 1 wherein said second polynucleotide sequence is (a).

3. The isolated nucleic acid molecule of claim 1 which comprises polynucleotide sequence (a).

4. The isolated nucleic acid molecule of claim 1 wherein said second polynucleotide sequence is (b).

5. The isolated nucleic acid molecule of claim 1 which comprises polynucleotide sequence (b).

6. The isolated nucleic acid molecule of claim 1 wherein said second polynucleotide sequence is (c).

7. The isolated nucleic acid molecule of claim 1 which comprises polynucleotide sequence (c).

8. The isolated nucleic acid molecule of claim 7 wherein said second polynucleotide sequence comprises nucleotides 212 to 1666 of SEQ ID NO:1.

9. The isolated nucleic acid molecule of claim 1 wherein said second polynucleotide sequence is (d).

10. The isolated nucleic acid molecule of claim 1 which comprises polynucleotide sequence (d).

11. An isolated nucleic acid molecule comprising a first polynucleotide sequence 95% or more identical to a second polynucleotide sequence selected from the group consisting of:

(a) a polynucleotide sequence encoding a DCDGF (Dendritic Cell-Derived Growth Factor) polypeptide having the complete amino acid sequence encoded by the cDNA clone contained in ATCC Deposit No. 97852;

(b) a polynucleotide sequence encoding the mature DCDGF polypeptide encoded by the cDNA clone contained in ATCC Deposit No. 97852; and (c) a polynucleotide sequence complementary to any of the polynucleotide sequences in (a) or (b) above;

wherein percentage identity is determined using the BESTFIT program with parameters that calculate identity over the full length of the second polynucleotide sequence and that allows gaps of up to 5% of the total number of nucleotides of said nucleotide sequence.

12. The isolated nucleic acid molecule of claim 11 wherein said second polynucleotide sequence is (a).

13. The isolated nucleic acid molecule of claim 11 which comprises polynucleotide sequence (a).

14. The isolated nucleic acid molecule of claim 11 wherein said second polynucleotide sequence is (b).

15. The isolated nucleic acid molecule of claim 11 which comprises polynucleotide sequence (b).

16. The isolated nucleic acid molecule of claim 11 wherein said second polynucleotide sequence is (c).

17. The isolated nucleic acid molecule of claim 11 which comprises polynucleotide sequence (c).

18. An isolated nucleic acid molecule comprising a first polynucleotide sequence 95% or more identical to a second polynucleotide sequence selected from the group consisting of:

(a) a polynucleotide sequence encoding a polypeptide comprising the amino acid sequence of residues n to 485 of SEQ ID NO:2, where n is any integer except zero in the range of −25 to +19;

(b) a polynucleotide sequence encoding a polypeptide comprising the amino acid sequence of residues −25 to m of SEQ ID NO:2, where m is any integer except zero in the range of 464 to 484; and (c) a polynucleotide sequence encoding a polypeptide having the amino acid sequence consisting of residues n to m of SEQ ID NO:2, where n and m are integers as defined respectively in (a) and (b) above;

wherein percentage identity is determined using the BESTFIT program with parameters that calculate identity over the full length of the second polynucleotide sequence and that allows gaps of up to 5% of the total number of nucleotides of said nucleotide sequence.

19. The isolated nucleic acid molecule of claim 18 wherein said second polynucleotide sequence is (a).

20. The isolated nucleic acid molecule of claim 18 which comprises polynucleotide sequence (a).

21. The isolated nucleic acid molecule of claim 20 which comprises a polynucleotide sequence encoding amino acids 19 to 485 of SEQ ID NO:2.

22. The isolated nucleic acid molecule of claim 18 wherein said second polynucleotide sequence is (b).

23. The isolated nucleic acid molecule of claim 18 which comprises polynucleotide sequence (b).

24. The isolated nucleic acid molecule of claim 18 wherein said second polynucleotide sequence is (c).

25. The isolated nucleic acid molecule of claim 18 which comprises polynucleotide sequence (c).

26. An isolated nucleic acid molecule encoding a fragment of amino acids 1 to 485 of SEQ ID NO:2, wherein said fragment binds an antibody specific to the polypeptide having amino acids 1 to 485 of SEQ ID NO:2.

27. An isolated nucleic acid encoding a polypeptide comprising 30 contiguous amino acids from amino acids 1 to 485 of SEQ ID NO:2.

28. The isolated nucleic acid of claim 27 which encodes a polypeptide comprising 50 contiguous amino acids from amino acids 1 to 485 of SEQ ID NO:2.

29. An isolated nucleic acid comprising 20 contiguous nucleotides from nucleotides 134 to 1666 of SEQ ID NO:1.

30. The isolated nucleic acid of claim 29 which comprises 30 contiguous nucleotides from nucleotides 134 to 1666 of SEQ ID NO:1.

31. The isolated nucleic acid of claim 29 which comprises 40 contiguous nucleotides from nucleotides 134 to 1666 of SEQ ID NO:1.

32. The isolated nucleic acid of claim 29 which comprises 50 contiguous nucleotides from nucleotides 134 to 1666 of SEQ ID NO:1.

33. An isolated nucleic acid molecule comprising a polynucleotide sequence selected from the group consisting of:

(a) a polynucleotide sequence encoding from amino acids 124 to 135 of SEQ ID NO.2;

(b) a polynucleotide sequence encoding from amino acids 139 to 149 of SEQ ID NO:2;

(c) a polynucleotide sequence encoding from amino acids 332 to 346 of SEQ ID NO:2;

(d) a polynucleotide sequence encoding from amino acids 371 to 379 of SEQ ID NO:2; and (e) a polynucleotide sequence encoding from amino acids 412 to 419 of SEQ ID NO:2.

34. The isolated nucleic acid molecule of claim 33 wherein said polynucleotide sequence is (a).

35. The isolated nucleic acid molecule of claim 33 wherein said polynucleotide sequence is (b).

36. The isolated nucleic acid molecule of claim 33 wherein said polynucleotide sequence is (c).

37. The isolated nucleic acid molecule of claim 33 wherein said polynucleotide sequence is (d).

38. The isolated nucleic acid molecule of claim 33 wherein said polynucleotide sequence is (e).

39. An isolated nucleic acid molecule comprising a first polynucleotide sequence which hybridizes to a second polynucleotide sequence complementary to nucleotides 134 to 1666 of SEQ ID NO:1, at 42° C. in a hybridization buffer consisting of 50% formamide, 5×SSC, 50 mM sodium phosphate (pH 7.6), 5×Denhardt's solution, 10% dextan sulfate, and 20 µg/ml denatured, sheared salmon sperm DNA, followed by washing in 0.1×SSC at 65° C.

40. The isolated nucleic acid molecule of claim 39 which encodes a polypeptide that binds an antibody specific to the polypeptide having amino acids 1 to 485 of SEQ ID NO:2.

41. The isolated nucleic acid molecule of claim 1 wherein said nucleic acid molecule comprises a heterologous polynucleotide sequence.

42. The isolated nucleic acid molecule of claim 41 wherein said heterologous polynucleotide sequence encodes a polypeptide, and wherein said second polynucleotide sequence is selected from the group consisting of:

(i) a polynucleotide sequence encoding amino acids −26 to 485 of SEQ ID NO:2;

(ii) a polynucleotide sequence encoding amino acids −25 to 485 of SEQ ID NO:2; and (iii) a polynucleotide sequence encoding amino acids 1 to 485 of SEQ ID NO:2.

43. The isolated nucleic acid molecule of claim 42 wherein said heterologous polynucleotide sequence encodes an Fc polypeptide.

44. A method for making a recombinant vector comprising inserting the isolated nucleic acid molecule of claim 1 into a vector.

45. A recombinant vector comprising the isolated nucleic acid molecule of claim 1.

46. The recombinant vector of claim 45 wherein said nucleic acid molecule is operably associated with a heterologous regulatory sequence that controls gene expression.

47. A recombinant host cell comprising the isolated nucleic acid molecule of claim 1.

48. The recombinant host cell of claim 47 wherein said nucleic acid molecule is operably associated with a heterologous regulatory sequence that controls gene expression.

49. A method for producing a polypeptide, comprising:

(a) culturing a host cell comprising the nucleic acid molecule of claim 1 under conditions suitable to produce the polypeptide encoded by said nucleic acid; and (b) recovering said polypeptide, and wherein said second polynucleotide sequence is selected from the group consisting of:

(i) a polynucleotide sequence encoding amino acids −26 to 485 of SEQ ID NO:2;

(ii) a polynucleotide sequence encoding amino acids −25 to 485 of SEQ ID NO:2; and (iii) a polynucleotide sequence encoding amino acids 1 to 485 of SEQ ID NO:2.

50. The isolated nucleic acid molecule of claim 11 wherein said nucleic acid molecule comprises a heterologous polynucleotide sequence.

51. The isolated nucleic acid molecule of claim 50 wherein said heterologous polynucleotide sequence encodes a polypeptide and wherein said second polynucleotide sequence is selected from the group consisting of:

(i) a polynucleotide sequence encoding a DCDGF polypeptide having the complete amino acid sequence encoded by the cDNA clone contained in ATCC Deposit No. 97852; and (ii) a polynucleotide sequence encoding the mature DCDGF polypeptide encoded by the cDNA clone contained in ATCC Deposit No. 97852.

52. The isolated nucleic acid molecule of claim 51 wherein said heterologous polynucleotide sequence encodes an Fc polypeptide.

53. A method for making a recombinant vector comprising inserting the isolated nucleic acid molecule of claim 11 into a vector.

54. A recombinant vector comprising the isolated nucleic acid molecule of claim 11.

55. The recombinant vector of claim 54 wherein said nucleic acid molecule is operably associated with a heterologous regulatory sequence that controls gene expression.

56. A recombinant host cell comprising the isolated nucleic acid molecule of claim 11.

57. The recombinant host cell of claim 56 wherein said nucleic acid molecule is operably associated with a heterologous regulatory sequence that controls gene expression.

58. A method for producing a polypeptide, comprising:
(a) culturing a host cell comprising the nucleic acid molecule of claim 11 under conditions suitable to produce the polypeptide encoded by said nucleic acid; and
(b) recovering said polypeptide and wherein said second polynucleotide sequence is selected from the group consisting of:
(i) a polynucleotide sequence encoding a DCDGF polypeptide having the complete amino acid sequence encoded by the cDNA clone contained in ATCC Deposit No. 97852; and
(ii) a polynucleotide sequence encoding the mature DCDGF polypeptide encoded by the cDNA clone contained in ATCC Deposit No. 97852.

59. The isolated nucleic acid molecule of claim 18 wherein said nucleic acid molecule comprises a heterologous polynucleotide sequence.

60. The isolated nucleic acid molecule of claim 59 wherein said heterologous polynucleotide sequence encodes a polypeptide.

61. The isolated nucleic acid molecule of claim 60 wherein said heterologous polynucleotide sequence encodes an Fc polypeptide.

62. A method for making a recombinant vector comprising inserting the isolated nucleic acid molecule of claim 18 into a vector.

63. A recombinant vector comprising the isolated nucleic acid molecule of claim 18.

64. The recombinant vector of claim 63 wherein said nucleic acid molecule is operably associated with a heterologous regulatory sequence that controls gene expression.

65. A recombinant host cell comprising the isolated nucleic acid molecule of claim 18.

66. The recombinant host cell of claim 65 wherein said nucleic acid molecule is operably associated with a heterologous regulatory sequence that controls gene expression.

67. A method for producing a polypeptide, comprising:
(a) culturing a host cell comprising the nucleic acid molecule of claim 18 under conditions suitable to produce the polypeptide encoded by said nucleic acid; and
(b) recovering said polypeptide.

68. The isolated nucleic acid molecule of claim 26 wherein said nucleic acid molecule comprises a heterologous polynucleotide sequence.

69. The isolated nucleic acid molecule of claim 68 wherein said heterologous polynucleotide sequence encodes a polypeptide.

70. The isolated nucleic acid molecule of claim 69 wherein said heterologous polynucleotide sequence encodes an Fc polypeptide.

71. A method for making a recombinant vector comprising inserting the isolated nucleic acid molecule of claim 26 into a vector.

72. A recombinant vector comprising the isolated nucleic acid molecule of claim 26.

73. The recombinant vector of claim 72 wherein said nucleic acid molecule is operably associated with a heterologous regulatory sequence that controls gene expression.

74. A recombinant host cell comprising the isolated nucleic acid molecule of claim 26.

75. The recombinant host cell of claim 74 wherein said nucleic acid molecule is operably associated with a heterologous regulatory sequence that controls gene expression.

76. A method for producing a polypeptide, comprising:
(a) culturing a host cell comprising the nucleic acid molecule of claim 26 under conditions suitable to produce the polypeptide encoded by said nucleic acid; and
(b) recovering said polypeptide.

77. The isolated nucleic acid molecule of claim 27 wherein said nucleic acid molecule comprises a heterologous polynucleotide sequence.

78. The isolated nucleic acid molecule of claim 77 wherein said heterologous polynucleotide sequence encodes a polypeptide.

79. The isolated nucleic acid molecule of claim 78 wherein said heterologous polynucleotide sequence encodes an Fc polypeptide.

80. A method for making a recombinant vector comprising inserting the isolated nucleic acid molecule of claim 27 into a vector.

81. A recombinant vector comprising the isolated nucleic acid molecule of claim 27.

82. The recombinant vector of claim 81 wherein said nucleic acid molecule is operably associated with a heterologous regulatory sequence that controls gene expression.

83. A recombinant host cell comprising the isolated nucleic acid molecule of claim 27.

84. The recombinant host cell of claim 83 wherein said nucleic acid molecule is operably associated with a heterologous regulatory sequence that controls gene expression.

85. A method for producing a polypeptide, comprising:
(a) culturing a host cell comprising the nucleic acid molecule of claim 27 under conditions suitable to produce the polypeptide encoded by said nucleic acid; and
(b) recovering said polypeptide.

86. The isolated nucleic acid molecule of claim 29 wherein said nucleic acid molecule comprises a heterologous polynucleotide sequence.

87. The isolated nucleic acid molecule of claim 86 wherein said heterologous polynucleotide sequence encodes a polypeptide.

88. The isolated nucleic acid molecule of claim 87 wherein said heterologous polynucleotide sequence encodes an Fc polypeptide.

89. A method for making a recombinant vector comprising inserting the isolated nucleic acid molecule of claim 29 into a vector.

90. A recombinant vector comprising the isolated nucleic acid molecule of claim 29.

91. The recombinant vector of claim 90 wherein said nucleic acid molecule is operably associated with a heterologous regulatory sequence that controls gene expression.

92. A recombinant host cell comprising the isolated nucleic acid molecule of claim 29.

93. The recombinant host cell of claim 92 wherein said nucleic acid molecule is operably associated with a heterologous regulatory sequence that controls gene expression.

94. A method for producing a polypeptide, comprising:
(a) culturing a host cell comprising the nucleic acid molecule of claim 29 under conditions suitable to produce the polypeptide encoded by said nucleic acid; and
(b) recovering said polypeptide.

95. The isolated nucleic acid molecule of claim 33 wherein aid nucleic acid molecule comprises a heterologous polynucleotide sequence.

96. The isolated nucleic acid molecule of claim 95 wherein said heterologous polynucleotide sequence encodes a polypeptide.

97. The isolated nucleic acid molecule of claim 96 wherein said heterologous polynucleotide sequence encodes an Fc polypeptide.

98. A method for making a recombinant vector comprising inserting the isolated nucleic acid molecule of claim 33 into a vector.

99. A recombinant vector comprising the isolated nucleic acid molecule of claim 33.

100. The recombinant vector of claim 99 wherein said nucleic acid molecule is operably associated with a heterologous regulatory sequence that controls gene expression.

101. A recombinant host cell comprising the isolated nucleic acid molecule of claim 33.

102. The recombinant host cell of claim 101, wherein said nucleic acid molecule is operably associated with a heterologous regulatory sequence that controls gene expression.

103. A method for producing a polypeptide, comprising:
(a) culturing a host cell comprising the nucleic acid molecule of claim 33 under conditions suitable to produce the polypeptide encoded by said nucleic acid; and
(c) recovering said polypeptide.

104. The isolated nucleic acid molecule of claim 39 wherein said nucleic acid molecule comprises a heterologous polynucleotide sequence.

105. The isolated nucleic acid molecule of claim 104 wherein said heterologous polynucleotide sequence encodes a polypeptide.

106. The isolated nucleic acid molecule of claim 105 wherein said heterologous polynucleotide sequence encodes an Fc polypeptide.

107. A method for making a recombinant vector comprising inserting the isolated nucleic acid molecule of claim 39 into a vector.

108. A recombinant vector comprising the isolated nucleic acid molecule of claim 39.

109. The recombinant vector of claim 108 wherein said nucleic acid molecule is operably associated with a heterologous regulatory sequence that controls gene expression.

110. A recombinant host cell comprising the isolated nucleic acid molecule of claim 39.

111. The recombinant host cell of claim 110 wherein said nucleic acid molecule is operably associated with a heterologous regulatory sequence that controls gene expression.

112. A method for producing a polypeptide, comprising:
(a) culturing a host cell comprising the nucleic acid molecule of claim 39 under conditions suitable to produce the polypeptide encoded by said nucleic acid; and
(b) recovering said polypeptide.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 3621 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 134..1666

(ix) FEATURE:
        (A) NAME/KEY: sig_peptide
        (B) LOCATION: 134..212

(ix) FEATURE:
        (A) NAME/KEY: mat_peptide
        (B) LOCATION: 215..1666

(xi) SEQUENCE DESCRIPTION: SEQ ID NO:1:

TCGACCCACG CGTCCGGCTT TTCCGGTGCT CTGCACAGAT GCTGGGCGC TGAGCAAACA    60

GCCCTCAGTT TCTGGAGCTG TTCCGAGTCC CGTGGAGTCT CCATCTGAGC CCTTTCCTAG    120

TCCAGGCATC CCG ATG TTG GTG GAT GGC CCA TCT GAG CGG CCA GCC CTG    169

```
                Met Leu Val Asp Gly Pro Ser Glu Arg Pro Ala Leu
                -26 -25             -20             -15

TGC TTC TTG CTG TTG GCT GTG GCA ATG TCT TTC TTC GGC TCA GCT CTA          217
Cys Phe Leu Leu Leu Ala Val Ala Met Ser Phe Phe Gly Ser Ala Leu
                -10             -5                       1

TCC ATA GAT GAA ACA CGG GCG CAT CTG TTG TTG AAA GAA AAG ATG ATG          265
Ser Ile Asp Glu Thr Arg Ala His Leu Leu Leu Lys Glu Lys Met Met
         5                   10                  15

CGG CTG GGG GGG CGG CTG GTG CTG AAT ACC AAG GAG GAG CTG GCC AAT          313
Arg Leu Gly Gly Arg Leu Val Leu Asn Thr Lys Glu Glu Leu Ala Asn
     20                  25                  30

GAG AGG CTC ATG ACG CTC AAA ATC GCT GAG ATG AAG GAG GCC ATG AGG          361
Glu Arg Leu Met Thr Leu Lys Ile Ala Glu Met Lys Glu Ala Met Arg
 35              40                  45                      50

ACC CTG ATA TTC CCA CCC AGC ATG CAC TTT TTC CAG GCC AAG CAT CTC          409
Thr Leu Ile Phe Pro Pro Ser Met His Phe Phe Gln Ala Lys His Leu
                 55                  60                  65

ATT GAG AGA AGT CAA GTG TTT AAT ATT CTA AGG ATG ATG CCA AAA GGG          457
Ile Glu Arg Ser Gln Val Phe Asn Ile Leu Arg Met Met Pro Lys Gly
         70                  75                  80

GCT GCC TTG CAC CTC CAT GAC ATT GGC ATC GTG ACT ATG GAC TGG CTG          505
Ala Ala Leu His Leu His Asp Ile Gly Ile Val Thr Met Asp Trp Leu
             85                  90                  95

GTG AGG AAT GTC ACC TAC AGG CCT CAC TGC CAC ATC TGT TTC ACC CCA          553
Val Arg Asn Val Thr Tyr Arg Pro His Cys His Ile Cys Phe Thr Pro
     100                 105                 110

AGG GGG ATC ATG CAG TTC AGA TTT GCT CAC CCA ACT CCC CGT CCA TCA          601
Arg Gly Ile Met Gln Phe Arg Phe Ala His Pro Thr Pro Arg Pro Ser
115             120                 125                     130

GAA AAA TGT TCC AAG TGG ATT CTG CTG GAG GAT TAT CGG AAG CGG GTG          649
Glu Lys Cys Ser Lys Trp Ile Leu Leu Glu Asp Tyr Arg Lys Arg Val
                 135                 140                 145

CAG AAC GTC ACT GAG TTT GAT GAC AGC TTG CTG AGG AAT TTC ACT CTG          697
Gln Asn Val Thr Glu Phe Asp Asp Ser Leu Leu Arg Asn Phe Thr Leu
         150                 155                 160

GTG ACC CAG CAC CCG GAG GTG ATT TAC ACA AAC CAA AAT GTT GTC TGG          745
Val Thr Gln His Pro Glu Val Ile Tyr Thr Asn Gln Asn Val Val Trp
             165                 170                 175

TCG AAA TTT GAA ACC ATC TTC TTC ACC ATC TCT GGT CTC ATC CAT TAC          793
Ser Lys Phe Glu Thr Ile Phe Phe Thr Ile Ser Gly Leu Ile His Tyr
    180                 185                 190

GCA CCA GTG TTC AGA GAC TAT GTC TTC CGG AGC ATG CAG GAG TTC TAC          841
Ala Pro Val Phe Arg Asp Tyr Val Phe Arg Ser Met Gln Glu Phe Tyr
195             200                 205                     210

GAG GAC AAC GTG CTC TAC ATG GAG ATC AGA GCC AGG CTG CTG CCG GTG          889
Glu Asp Asn Val Leu Tyr Met Glu Ile Arg Ala Arg Leu Leu Pro Val
         215                 220                 225

TAT GAG CTC AGT GGA GAG CAC CAT GAC GAA GAG TGG TCA GTG AAG ACT          937
Tyr Glu Leu Ser Gly Glu His His Asp Glu Glu Trp Ser Val Lys Thr
             230                 235                 240

TAC CAG GAA GTA GCT CAG AAG TTT GTG GAA ACT CAC CCT GAG TTT ATT          985
Tyr Gln Glu Val Ala Gln Lys Phe Val Glu Thr His Pro Glu Phe Ile
        245                 250                 255

GGA ATC AAA ATC ATT TAT TCG GAT CAC AGA TCC AAA GAT GTG GCT GTC         1033
Gly Ile Lys Ile Ile Tyr Ser Asp His Arg Ser Lys Asp Val Ala Val
260             265                 270

ATC GCA GAA TCC ATC CGA ATG GCC ATG GGG CTC CGA ATC AAG TTC CCC         1081
Ile Ala Glu Ser Ile Arg Met Ala Met Gly Leu Arg Ile Lys Phe Pro
275             280                 285                 290

ACG GTG GTG GCA GGG TTT GAC CTG GTG GGG CAT GAG GAC ACT GGC CAC         1129
```

```
         Thr Val Val Ala Gly Phe Asp Leu Val Gly His Glu Asp Thr Gly His
                     295                 300                 305

TCC TTG CGT GAC TAC AAG GAA GCT CTG ATG ATC CCC GCC AAG GAT GGC        1177
         Ser Leu Arg Asp Tyr Lys Glu Ala Leu Met Ile Pro Ala Lys Asp Gly
                     310                 315                 320

GTT AAG CTG CCT TAC TTC TTC CAC GCC GGA GAA ACA GAC TGG CAG GGT        1225
         Val Lys Leu Pro Tyr Phe Phe His Ala Gly Glu Thr Asp Trp Gln Gly
                     325                 330                 335

ACT TCC ATA GAC AGG AAC ATT CTG GAT GCT CTG ATG CTG AAC ACT ACC        1273
         Thr Ser Ile Asp Arg Asn Ile Leu Asp Ala Leu Met Leu Asn Thr Thr
                     340                 345                 350

AGA ATC GGC CAT GGA TTT GCT TTG AGC AAA CAC CCC GCA GTC AGG ACT        1321
         Arg Ile Gly His Gly Phe Ala Leu Ser Lys His Pro Ala Val Arg Thr
         355                 360                 365                 370

TAC TCC TGG AAA AAG GAC ATC CCC ATA GAA GTC TGT CCC ATC TCT AAC        1369
         Tyr Ser Trp Lys Lys Asp Ile Pro Ile Glu Val Cys Pro Ile Ser Asn
                     375                 380                 385

CAG GTG CTG AAA CTG GTG TCT GAC TTG AGG AAC CAC CCT GTA GCC ACT        1417
         Gln Val Leu Lys Leu Val Ser Asp Leu Arg Asn His Pro Val Ala Thr
                     390                 395                 400

CTG ATG GCC ACT GGG CAC CCC ATG GTG ATC AGC TCT GAT GAC CCA GCT        1465
         Leu Met Ala Thr Gly His Pro Met Val Ile Ser Ser Asp Asp Pro Ala
                     405                 410                 415

ATG TTT GGT GCC AAA GGC TTG TCC TAT GAT TTC TAT GAG GTC TTC ATG        1513
         Met Phe Gly Ala Lys Gly Leu Ser Tyr Asp Phe Tyr Glu Val Phe Met
                     420                 425                 430

GGC ATT GGG GGG ATG AAG GCT GAC CTG AGG ACC CTC AAA CAG CTG GCC        1561
         Gly Ile Gly Gly Met Lys Ala Asp Leu Arg Thr Leu Lys Gln Leu Ala
         435                 440                 445                 450

ATG AAC TCT ATC AAG TAC AGT ACC CTG TTG GAG AGT GAG AAA AAT ACT        1609
         Met Asn Ser Ile Lys Tyr Ser Thr Leu Leu Glu Ser Glu Lys Asn Thr
                     455                 460                 465

TCC ATG GAA ATC TGG AAG AAG AGA TGG GAT AAG TTC ATA GCA GAT GTG        1657
         Ser Met Glu Ile Trp Lys Lys Arg Trp Asp Lys Phe Ile Ala Asp Val
                     470                 475                 480

GCT ACA AAG TGAGGAGAAG CTAGCCAGCC CTCTACAAGC TGTCTTCTTG                1706
         Ala Thr Lys
                485

CACACGCTGT CACTTCCTCT CACTCGTTCT TGAATCAGCT CCATGTGCCC ATGAAATCAA       1766

TGGCCTCTGT ATGGAGCGAC CCTGTGAGAA GCACTTGGCT GGCTGAACAA ATTCATCCTC       1826

TGGAAATATT CTCTCTCAGC CACAGTGACA TTGACCTCTT GGTTTTCTCC TCTCTCTGGC       1886

CATTTCTTCC AGTTTCCCTA TTTCAGAGTC TTCTCCTCTC TCTGATCTCT GTGCTGTTTC       1946

CTCAGGACTC AGTCCTGGGC TCTCTTCTAT TCTGGTCTCT TTATTTTTTT ATTTTTGTAT       2006

TTTTTCGAGA TGGAGTTTTG CTCTTGTTGC CCAGGCTGGA GTACAATGGT GCGATCTCAG       2066

CTCAGTGCAA CCTCCGCCAC CCGGGTTCAG GCAATTCTCT TGCATCAGCC TCGCGAGTAG       2126

TTGGAATTAT AGGCATGTGC CACCACACCC AGCTGATTTT TGCATTTTTA GTAGAGACAG       2186

GTTTTCACCA TGTTGGCGAG GCTGGTATCC AACTCTTGAC CTCAGGTGAT CCACTCGCCC       2246

CTTGGCTCCC AAAGTGCTGG AATTACAGGC ATTAGCCACC ATGCCTGGCC TATTCTGGTC       2306

TCTTTAACTC TCTCCTCTTT ATTTCTCTTC TCTCTCTGTA CACTTTTCCT GGGTGGTCTC       2366

ATCCATTCCT TTGCTTTTTC ATACCATTTA TTTGTTAATG ATTCCCACAT TTATTTATGC       2426

ACTTGGAGAG CTCACAGGAA TCTCAGAAAC TGATGAGGTA CAATTCTGAA CCCTCAGTCT       2486

CTTCCCTTTA AACCTTTCTT TTTCTCTACT TTAATTTTTC TAAAGATGTC TTGCTATGTT       2546

GCCCAGGCTG GTCTCCAACT CAAGTGATCC TCCTGCCGCA GTCTCCCGAA GTGCTGGGAT       2606
```

-continued

```
TACTGACATG AGCCACCACA CTCAGCCCTT TAAACCTTTC CCTGGCCTTT CCCATAGCTG      2666

GTGAAGGACA CCTCCATCCA TTCCACGCAG TTGCTCAAAG CAGAAATTTT CAGTGCAAGT      2726

CTTGATGCTG CGCCGTCCCC CACTCCCTAC ATCAGAACGC ATCCCTCATC TGGACTCCAG      2786

CGGTGGCTTC TTGATGCTGC GCGGTCCCCC ACTCCCTACA TCAGAATGCA TCCCGCATCC      2846

AGACTCCAGC GGTGGTGCTC TACCTGCACG CTGTTGCCAA GTCCAAGCTA CCATACTCCT      2906

GCCTGAGCTA TGACAACAGC CTCCTCACTG ATCTCCCCTT TCTTCCCTTT GCCTCCTCCA      2966

GCTCATTTTT CACAGTGGTA GAATGACATT TTGTTTGTTT GTTTTGTTTT GTTTGGGATG      3026

GAGTCTCGCT CTGTTGCCCA GGGTGGAGTG CAGCGGTGCG ATCTCGGCTC ACTGCAACCT      3086

CCACCTCCCG GGTTCAGGCG GATTCTCGTG CCTCAGCCTC CTGAGTAGCT GGGATTACAG      3146

GCATGCACCA CCATGCCCGG ATAATTTTTG TGTTTTTAGT AAAAATGGGG TTTCACTGTG      3206

TTGGCAGGCT GGTCTCGAAC ACCTGACTCG TGGTCCACCC GCCTCGGCCT CCCAAAGCAC      3266

TGGGATTGCA GGCGTAGCCA CCCGGCTGCC TAGAATAGAC TTTTAGAAAT CAAAATAATC      3326

AGGTGTCTCC TTCGCATACA CCCTCGTCCA AGTACACCCC ATGTCTCCAC GGGCATACAC      3386

CATCCAATGT AATCTGGATT CATTCCGGCG CTCCTCTCCA TATCAAGGGC CCCAACCCCG      3446

GCGGACGTCT CTCAAAGTCC ACGCTCTATA CCGTGCCTGG TCTTTCTCTT TCTCTCTCCT      3506

GAAAAAGTCA TGTTCTCTAT TCTTGCCCAA TCCTGTTTAC CTAAATTTTC AAGTTCAATT      3566

TAGTCTCAGA AAAGTTTCCT GTGCCCCCAT TCTCCAGAAA GCAGCCCCTT GCCGC           3621
```

(2) INFORMATION FOR SEQ ID NO:2:

(i) SEQUENCE CHARACTERISTICS:
        (A) LENGTH: 511 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Val Asp Gly Pro Ser Glu Arg Pro Ala Leu Cys Phe Leu Leu
-26 -25                 -20                 -15

Leu Ala Val Ala Met Ser Phe Phe Gly Ser Ala Leu Ser Ile Asp Glu
-10              -5                   1                   5

Thr Arg Ala His Leu Leu Lys Glu Lys Met Met Arg Leu Gly Gly
                10                  15                  20

Arg Leu Val Leu Asn Thr Lys Glu Glu Leu Ala Asn Glu Arg Leu Met
            25                  30                  35

Thr Leu Lys Ile Ala Glu Met Lys Glu Ala Met Arg Thr Leu Ile Phe
        40                  45                  50

Pro Pro Ser Met His Phe Phe Gln Ala Lys His Leu Ile Glu Arg Ser
55                  60                  65                  70

Gln Val Phe Asn Ile Leu Arg Met Met Pro Lys Gly Ala Ala Leu His
                75                  80                  85

Leu His Asp Ile Gly Ile Val Thr Met Asp Trp Leu Val Arg Asn Val
                90                  95                  100

Thr Tyr Arg Pro His Cys His Ile Cys Phe Thr Pro Arg Gly Ile Met
            105                 110                 115

Gln Phe Arg Phe Ala His Pro Thr Pro Arg Pro Ser Glu Lys Cys Ser
        120                 125                 130

Lys Trp Ile Leu Leu Glu Asp Tyr Arg Lys Arg Val Gln Asn Val Thr
135                 140                 145                 150
```

Glu Phe Asp Asp Ser Leu Leu Arg Asn Phe Thr Leu Val Thr Gln His
                155                 160                 165

Pro Glu Val Ile Tyr Thr Asn Gln Asn Val Val Trp Ser Lys Phe Glu
            170                 175                 180

Thr Ile Phe Phe Thr Ile Ser Gly Leu Ile His Tyr Ala Pro Val Phe
        185                 190                 195

Arg Asp Tyr Val Phe Arg Ser Met Gln Glu Phe Tyr Glu Asp Asn Val
    200                 205                 210

Leu Tyr Met Glu Ile Arg Ala Arg Leu Leu Pro Val Tyr Glu Leu Ser
215                 220                 225                 230

Gly Glu His His Asp Glu Trp Ser Val Lys Thr Tyr Gln Glu Val
                235                 240                 245

Ala Gln Lys Phe Val Glu Thr His Pro Glu Phe Ile Gly Ile Lys Ile
            250                 255                 260

Ile Tyr Ser Asp His Arg Ser Lys Asp Val Ala Val Ile Ala Glu Ser
        265                 270                 275

Ile Arg Met Ala Met Gly Leu Arg Ile Lys Phe Pro Thr Val Val Ala
    280                 285                 290

Gly Phe Asp Leu Val Gly His Glu Asp Thr Gly His Ser Leu Arg Asp
295                 300                 305                 310

Tyr Lys Glu Ala Leu Met Ile Pro Ala Lys Asp Gly Val Lys Leu Pro
                315                 320                 325

Tyr Phe Phe His Ala Gly Glu Thr Asp Trp Gln Gly Thr Ser Ile Asp
            330                 335                 340

Arg Asn Ile Leu Asp Ala Leu Met Leu Asn Thr Thr Arg Ile Gly His
        345                 350                 355

Gly Phe Ala Leu Ser Lys His Pro Ala Val Arg Thr Tyr Ser Trp Lys
    360                 365                 370

Lys Asp Ile Pro Ile Glu Val Cys Pro Ile Ser Asn Gln Val Leu Lys
375                 380                 385                 390

Leu Val Ser Asp Leu Arg Asn His Pro Val Ala Thr Leu Met Ala Thr
                395                 400                 405

Gly His Pro Met Val Ile Ser Ser Asp Asp Pro Ala Met Phe Gly Ala
            410                 415                 420

Lys Gly Leu Ser Tyr Asp Phe Tyr Glu Val Phe Met Gly Ile Gly Gly
        425                 430                 435

Met Lys Ala Asp Leu Arg Thr Leu Lys Gln Leu Ala Met Asn Ser Ile
    440                 445                 450

Lys Tyr Ser Thr Leu Leu Glu Ser Glu Lys Asn Thr Ser Met Glu Ile
455                 460                 465                 470

Trp Lys Lys Arg Trp Asp Lys Phe Ile Ala Asp Val Ala Thr Lys
                475                 480                 485

(2) INFORMATION FOR SEQ ID NO:3:

(i) SEQUENCE CHARACTERISTICS:
        (A) LENGTH: 516 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Val Phe Ala His Asn Glu Ala Arg Arg Ala Ser Leu Arg Ala Asn His
1               5                   10                  15

Met Val Gln His Ala Pro His Ile Glu Pro Gln Ala Ser Val Ile Gly

```
                    20                  25                  30
Gly Arg Pro Thr Pro Glu Ala Tyr Asn Ser Leu Arg Asp Ile Phe Phe
            35                  40                  45
Arg Tyr Glu Glu Ser Lys Thr Leu Gly Ala Asp Ile Thr Leu Thr Gln
 50                  55                  60
Lys Glu Leu Gln Ala Asn Gln Leu Ile Met Glu Ala Lys Thr Arg Glu
 65                  70                  75                  80
Tyr Glu Glu Gly Leu Ala Thr Pro His Leu Phe Thr Pro Ser Gln His
                85                  90                  95
Leu Phe Glu Val Leu Asp Asp Ile Lys Gln Ser Pro Leu Phe Lys Tyr
                100                 105                 110
Ile Ser Ser Met Pro Lys Gly Ala Val Leu His Ala His Asp Thr Ala
                115                 120                 125
Leu Cys Ser Thr Asp Phe Leu Ile Arg Leu Thr Tyr Arg Asp Asn Leu
    130                 135                 140
Trp Val Cys Gln Gly Lys Gly Asp Lys Glu Val Ile Gly Met Arg Phe
145                 150                 155                 160
Ser Lys Thr Lys Pro Asp Val Ala Thr Gln Ala Asp Cys Thr Trp Glu
                165                 170                 175
Leu Leu Ser Lys Val Arg Glu Leu His Gly Ala Asp Lys Val Asp Thr
                180                 185                 190
Tyr Leu Arg Glu His Leu Thr Leu Tyr Pro Thr Val Lys Phe Leu Asp
                195                 200                 205
Asn Asn Glu Ala Trp Glu Gln Phe Gly Ser Ile Phe Ala Leu Leu Asp
    210                 215                 220
Gly Leu Leu Phe Tyr Ala Pro Ser Trp Ala Asp Tyr Tyr Asn Ala
225                 230                 235                 240
Leu Lys Glu Phe His Ala Asp Gly Val Gln Tyr Leu Glu Phe Arg Ser
                245                 250                 255
Thr Leu Pro Ile Leu Tyr Asp Leu Glu Gly Thr Ser Phe Thr Glu Leu
                260                 265                 270
Asp Thr Val Arg Ile Tyr Lys Gly Thr Leu Asp Lys Tyr Met Ala Glu
                275                 280                 285
His Ile Asp Phe Ile Gly Ser Lys Leu Ile Tyr Ala Pro Ile Arg Asn
    290                 295                 300
Thr Asp Lys Glu Gly Leu Asp Asn Tyr Ile Lys Val Cys Val Glu Ile
305                 310                 315                 320
Lys Glu Lys Tyr Pro Asp Phe Val Ala Gly Phe Asp Leu Val Gly Gln
                325                 330                 335
Glu Glu Lys Gly Arg Pro Leu Lys Asp Phe Ile Pro Gln Leu Leu Gly
                340                 345                 350
Met Pro Glu Asn Ile Asp Phe Tyr Phe His Ala Gly Glu Thr Asn Trp
                355                 360                 365
Phe Gly Ser Thr Val Asp Glu Asn Leu Ile Asp Ala Val Leu Leu Gly
    370                 375                 380
Thr Lys Arg Ile Gly His Gly Phe Ala Leu Val Lys His Pro Leu Val
385                 390                 395                 400
Leu Gln Met Leu Lys Glu Arg Asn Ile Ala Ile Glu Val Asn Pro Ile
                405                 410                 415
Ser Asn Gln Val Leu Gln Leu Val Ala Asp Tyr Arg Asn His Pro Cys
                420                 425                 430
Ala Tyr Phe Phe Ala Asp Asn Tyr Pro Val Val Ile Ser Ser Asp Asp
                435                 440                 445
```

```
Pro Ser Phe Trp Lys Ala Thr Pro Leu Ser His Asp Phe Tyr Ile Ala
450                 455                 460

Phe Leu Gly Ile Ala Ser Ala His Ser Asp Met Arg Leu Leu Lys Lys
465                 470                 475                 480

Leu Ala Leu Asn Ser Ile Asn Tyr Ser Ser Leu Ser Pro Glu Gln Lys
                485                 490                 495

Arg Val Ala Leu Ala Lys Trp Gln Ile Lys Trp Asp Asp Phe Ile Asp
                500                 505                 510

Glu Val Leu Ser
        515

(2) INFORMATION FOR SEQ ID NO:4:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ATGTTGGTGG ATGGCCCATC TGAGCGGCCA GCCCTGTGCT TCTTGCTGTT GGCTGTGGCA        60

ATGTNTTTNT TCGGCTCAGC TCTATCCATA GATGAAACAC GGGCGCATCT NTTGTTGAAA       120

GAAAAGATGA TGCGGCTCGG GGGGCGGCTG GTGCTGAACA CCAAGGAGGA GCTGGCCAAT       180

NAGAGGCTCA TGACGCTCAA AATCGCTGAG ATGAAGGAGG CCATGAGGAC CCTGATATTC       240

CCACCCAGCA TGCACTTTTT TCCAGG                                           266

(2) INFORMATION FOR SEQ ID NO:5:

(i) SEQUENCE CHARACTERISTICS:
        (A) LENGTH: 491 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AATTCGGCAN AGCCCAGAGA GCATCTGGNT TCAATTTTCC TTTTTCCGGN GGGAGTATNG        60

ATTCCCTGGA ATGGAACTGG GCTCTGGTGT ATGAGCTCAN TGGAGAGCAC CATGACGAGA       120

AGTGGTCAGT GAAGACTTAC CAGGTAAGTA GCTCAGAAGT TTGTGGAAAC TCACCCTGAG       180

TTTATTGGAA TCAAAATCAT TTATTCGGAT CACAGATCCA AAGATGTGGC TGTCATCGCA       240

GAATCCATCC GAATNGCCAT GGGNCTNCGA ATNAATTCCC CACGGTTGGT GGTCAGGGTT       300

TGACCTTGTG GGGCATGAGG ACACTGGCCA TTNTTNCGTG ACTACAAGGA AGTTTGATGG       360

TTCNCGGCCA NGNTTGGGTT TAAGTNGNTT AATTTTTCCA NGCNGGNGAA NCANNTNGGT       420

AGGTATTNNC TTAGNNAGGA ACATTTNGGG TNNTTNGNTN GTGNACATTN CAGATGGGGC       480

ATGGGTTNGN T                                                           491

(2) INFORMATION FOR SEQ ID NO:6:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:6:

```
GGCACGAGCC GGAGAAACAG ACTGGCAGGG TACTTCCATA GACAGGAACA TTCTGGATGC      60

TCTGATGCTG AACACTACCA GAATCGGCCA TGGATTTGCT TTGAGCAAAC ACCCCGCAGT     120

CAGGACTTAC TCCTGGAAAA AGGACATCCC CATAGAAGTC TGTCCCATCT CTAACCAGGT     180

GCTGAAACTG GTGTCTGACT TGAGGAACCA CCCTGTAGCC ACTCTGATGG CCACTGGGCA     240

CCCCATGGTG ATCAGCTCTG ATGACCCAGC TATGTTTGGT GCCAAAGGTT TGTCCTACGG     300

ATTTCTATGA GGTCTTCATG GGCATTGGGG GGNTGAAGGT TGACCTGAGG ACCCTCAAAC     360

AGTTGGNCAT GAANTTTNTC AATACANTTA CC                                   392
```

(2) INFORMATION FOR SEQ ID NO:7:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
AGGTTACAGT ACCCTNTTGG AGAGTGAGAA AAATACTTTC ATGGAAATCT GGAAGAAGAG      60

ATGGGATAAG TTCATAGCAG ATGTGGCTAC AAAGTGAGGA GAAGCTAGCC AGCCCTCTAC     120

AAGCTGTCTT CTTGCACACG CTGTCACTTC CTNTCACTCG TTCTTGGAAT CAGCTCCATG     180

TGCCCATGAA ATCAATGGCC TCTGTATGGA GCGACCCTGT GAGNNGCACT TGGCTGGCTG     240

AGCAAATTCA TCCTCTGGAA ATAATTCTTT CTCAGCCACA GTGGACATTG ACCCTCTTGG     300

TTTTCTTCTN TCTNTGGGNA TTTCTTTCCA GTTTNCCTAT TTCAGAGTCT TCTCCTCTCT     360

NTGGTNTTNT GTGCTGGTTT CCCAGGATTC ATCCCGGGNT CTTTTCTATT CTGGNCCCTT     420

TAATTTNTAA ATTTGGAATT TTCGGGAAGG GTTTTGCCTT TGCCCAGTT GGGTANAAGG      480

GGGGTTTAAG TNAAGG                                                     496
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CATGGATCCA GCTCTATCCA TAGATGAAAC ACG                                   33
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GCAAAGCTTG GCTAGCTTCT CCTCACTTTG                                       30
```

(2) INFORMATION FOR SEQ ID NO:10:

```
        (i) SEQUENCE CHARACTERISTICS:
             (A) LENGTH: 37 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:10:

CTAGGATCCG CCATCATGTT GGTGGATGGC CCATCTG                                37

(2) INFORMATION FOR SEQ ID NO:11:

(i) SEQUENCE CHARACTERISTICS:
             (A) LENGTH: 30 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:11:

GCATCTAGAG GCTAGCTTCT CCTCACTTTG                                        30
```